United States Patent
Uno et al.

(10) Patent No.: US 10,208,101 B2
(45) Date of Patent: Feb. 19, 2019

(54) RECOMBINANT FIBRINOGEN HIGH-PRODUCTION LINE AND METHOD FOR PRODUCING SAME

(71) Applicant: JAPAN BLOOD PRODUCTS ORGANIZATION, Tokyo (JP)

(72) Inventors: Shusei Uno, Tokyo (JP); Momoko Otaki, Tokyo (JP); Kouji Murakami, Tokyo (JP); Shoji Ideno, Tokyo (JP)

(73) Assignee: JAPAN BLOOD PRODUCTS ORGANIZATION, Tokyo (JP)

( * ) Notice: Subject to any disclaimer, the term of this patent is extended or adjusted under 35 U.S.C. 154(b) by 284 days.

(21) Appl. No.: 15/108,194

(22) PCT Filed: Dec. 26, 2014

(86) PCT No.: PCT/JP2014/084516
§ 371 (c)(1),
(2) Date: Jun. 24, 2016

(87) PCT Pub. No.: WO2015/099124
PCT Pub. Date: Jul. 2, 2015

(65) Prior Publication Data
US 2016/0318990 A1    Nov. 3, 2016

(30) Foreign Application Priority Data
Dec. 27, 2013   (JP) .................................. 2013-273145

(51) Int. Cl.
*C07K 14/75* (2006.01)
*C07K 14/81* (2006.01)

(52) U.S. Cl.
CPC .......... *C07K 14/75* (2013.01); *C07K 14/8121* (2013.01); *C07K 14/8132* (2013.01); *C12N 2510/02* (2013.01); *C12N 2511/00* (2013.01)

(58) Field of Classification Search
None
See application file for complete search history.

(56) References Cited

U.S. PATENT DOCUMENTS

| | | |
|---|---|---|
| 6,037,457 A | 3/2000 | Lord |
| 2005/0080009 A1 | 4/2005 | Metzner et al. |
| 2010/0151522 A1 | 6/2010 | Matsuyama et al. |
| 2011/0177524 A1 | 7/2011 | Bout et al. |

FOREIGN PATENT DOCUMENTS

| | | |
|---|---|---|
| JP | 2004-016055 A | 1/2004 |
| JP | 2004-075682 A | 3/2004 |
| JP | 2011-527190 A | 10/2011 |
| WO | WO 2000/030436 A1 | 6/2000 |
| WO | WO 2005/010178 A1 | 2/2005 |

OTHER PUBLICATIONS

Binnie et al., "Characterization of Purified Recombinant Fibrinogen: Partial Phosphorylation of Fibrinopeptide A," *Biochemistry*, 32(1): 107-113 (1993).
Wright et al., "Fibrinolysis during normal human pregnancy: complex inter-relationships between plasma levels of tissue plasminogen activator and inhibitors and the euglobulin clot lysis time," *British Journal of Haematology*, 69(2): 253-258 (1988).
Japanese Patent Office, International Search Report in International Patent Application No. PCT/JP2014/084516 (dated Mar. 31, 2015).
Ritchie et al., "Cross-linking of Plasminogen Activator Inhibitor 2 and $\alpha_2$-Antiplasmin to Fibrin(ogen)," *The Journal of Biological Chemistry*, 275(32): 24915-24920 (2000).

*Primary Examiner* — Suzanne M Noakes
(74) *Attorney, Agent, or Firm* — Leydig, Voit & Mayer, Ltd.

(57) ABSTRACT

The present invention provides a recombinant strain highly producing fibrinogen which is an animal cell strain coexpressing a fibrinogen and an α2PI and/or PAI-2, genes encoding Aα chain, Bβ chain and γ chain of fibrinogen, a production method of a recombinant strain highly producing fibrinogen, including introducing gene(s) encoding α2PI and/or PAI-2 into an animal cell, and coexpressing fibrinogen and α2PI and/or PAI-2 in the animal cell, and a production method of a recombinant fibrinogen including culturing a recombinant strain highly producing fibrinogen in a medium, and recovering fibrinogen from the obtained culture.

10 Claims, 12 Drawing Sheets

Specification includes a Sequence Listing.

rFbg concentration

RECOMBINANT FIBRINOGEN HIGH-PRODUCTION LINE AND METHOD FOR PRODUCING SAME

CROSS-REFERENCE TO RELATED APPLICATIONS

This patent application is the U.S. national phase of International Patent Application No. PCT/JP2014/084516, filed Dec. 26, 2014, which claims the benefit of Japanese Patent Application No. 2013-273145, filed on Dec. 27, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 3,897 bytes ASCII (Text) file named "725796SequenceListing.txt," created Jun. 23, 2016.

TECHNICAL FIELD

The present invention relates to a recombinant strain highly producing fibrinogen and a production method thereof, as well as a production method of a recombinant fibrinogen by using said producing strain. More particularly, the present invention relates to a recombinant strain highly producing fibrinogen which is an animal cell strain coexpressing a fibrinogen and an α2 plasmin inhibitor (hereinafter to be also referred to as α2PI) and/or a plasminogen activator inhibitor 2 (hereinafter to be also referred to as PAI-2), genes encoding Aα chain, Bβ chain and γ chain of fibrinogen, a production method of a recombinant strain highly producing fibrinogen, comprising introducing gene(s) encoding α2PI and/or PAI-2 into an animal cell, and coexpressing fibrinogen and α2PI and/or PAI-2 in the animal cell, and a production method of a recombinant fibrinogen comprising culturing a recombinant strain highly producing fibrinogen in a medium, and recovering fibrinogen from the obtained culture.

BACKGROUND ART

Fibrinogen is one of the plasma glycoproteins mainly produced by liver (parenchymal) cell, and is a macromolecular glycoprotein having two each of 3 different kinds of polypeptide chains called Aα chain, Bβ chain and γ chain (6 chains in total). The molecular weight of each polypeptide chain is about 67,000 for Aα chain, about 56,000 for Bβ chain, and about 47,500 for γ chain, and a complete fibrinogen molecule composed of these chains associated via a disulfide bond has a molecular weight of about 340,000 (patent document 1).

Fibrinogen is an important protein present in normal plasma at 2-3 g/L, which exhibits defense and hemostasis functions in living organisms by inducing, when tissues are damaged, adhesion of platelets to the wound and subsequent hematological gelation. Therefore, when the fibrinogen level in blood decreases due to massive bleeding, severe infections and the like, the hemostasis mechanism collapses and bleeding cannot be suppressed to cause bleeding tendency, which is life-threatening.

Fibrinogen preparation is effective for preventing serious bleeding by increasing the fibrinogen concentration in blood by intravenous administration and the like, and is widely applied to a replacement therapy of congenital and acquired fibrinogen deficiency and the like. Also, fibrinogen is widely used as a main component of fibrin adhesive to be used for adhesion and closing of tissue during surgery.

At present, fibrinogen used as pharmaceutical products is mainly prepared from human pooled plasma collected from an unspecified large number (several thousand or more) of blood donors, and subjected to various pathogens inactivating, removing methods such as a tri-n-butyl phosphate (TNBP)/polysorbate 80 treatment, a filtration treatment with a virus removal membrane, a heat treatment and the like in an attempt to eliminate the risk of contamination with infectious agents such as hepatitis virus (e.g., HCV and the like), immunodeficient virus (e.g., HIV and the like), abnormal prion and the like. However, no matter how much the safety measure is taken, the risk of disease transmission due to the use of blood as a starting material cannot be eliminated completely. When a fibrinogen preparation derived from human pooled plasma is used, therefore, it is necessary to consider the effect provided and the risk of disease transmission and the like, sufficiently study the need thereof, use only in the minimum necessary amount, and sufficiently observe the progress after administration. Furthermore, since human pooled plasma is mainly supplied by blood donation, stable supply of fibrinogen in the future is also questioned.

To solve these problems, production of fibrinogen by utilizing a gene recombination technique has been tried. However, fibrinogen has not been placed in the market as a recombinant pharmaceutical product, even though plasmaproteins such as factor VIII, factor IX, albumin and the like have already been placed in the market as recombinant pharmaceutical products.

One of the causes preventing the development is the fact that fibrinogen is a huge protein molecule having an association of 6 polypeptide chains, and a functional fibrinogen molecule is difficult to produce even when 3 proteins of fibrinogen Aα chain, Bβ chain and γ chain are simultaneously expressed in *Escherichia coli*, and that a functional fibrinogen molecule can be produced in yeast and animal cells but production in a sufficient amount is not attainable, which in turn prevents practicalization from the aspect of production cost (non-patent document 1, patent documents 1 and 2).

Another cause is the fact that, when fibrinogen is expressed and cultured in animal cells, degradation of fibrinogen markedly progresses in the later stage of culture. Generally, cultured cells grow in the order of lag phase, logarithmic growth phase, stationary phase, and death phase, and the number of cultured cells and the production amount of recombinant protein are correlated. Therefore, when a recombinant protein is produced, it is considered that an extension of the period of stationary phase when the number of cultured cells reaches the peak, i.e., the later stage of culture, leads to an increase in the production amount of the recombinant protein. Remarkable degradation of fibrinogen in the later stage of culture is a fatal problem for mass production of fibrinogen, and renders the production of high quality recombinant fibrinogen in a high yield even more difficult.

Plasmin is a serine protease that hydrolyzes fibrinogen and fibrin produced from fibrinogen (dissolve of fibrin: fibrinolysis). In the fibrinolytic system, plasminogen is restrictively degraded by a plasminogen activator to be a plasmin having an enzyme activity, which shows a function to mainly dissolve fibrin thrombus.

An α2 plasmin inhibitor (α2PI) is a main inhibitory factor of plasmin which takes charge of the fibrinolytic system, and is a protein that specifically binds to plasmin at a ratio of 1:1 to form a plasmin-α2PI complex (PIC), which rapidly deactivates the plasmin activity.

Plasminogen activator inhibitors (PAI)-1 and PAI-2 are inhibitors belonging to the serine protease inhibitor superfamily (SERPIN) and present in vivo. It is a protein that suppresses generation of plasmin from plasminogen by inhibiting the plasminogen activator. It has been reported that PAI-1 is present in normal plasma at a concentration of about 20 ng/mL, whereas PAI-2 is generally undetectable in non-pregnant plasma (non-patent document 2).

However, the relationship between α2PI and/or PAI-2, and a fibrinogen production-enhancing effect in recombinant fibrinogen producing cells has not been reported at all, and the effect thereof is unknown.

DOCUMENT LIST

Patent Documents patent document 1: U.S. Pat. No. 6,037,457
patent document 2: JP-A-2004-16055

Non-Patent Documents non-patent document 1: Binnie et al., Biochemistry 32, 107(1993)
non-patent document 2: Wright J G et al., Br J Haematol 69,253 (1988)

SUMMARY OF THE INVENTION

Problems to be Solved by the Invention

Since fibrinogen currently used as a pharmaceutical product is mainly prepared from human pooled plasma, sufficient safety cannot be secured, and stable supply is also questioned. To solve these problems, production of fibrinogen by a gene recombination technique has been tried, but a sufficient production amount has not been afforded, and practicalization has not been realized due to the production costs.

It is therefore an object of the present invention to provide a recombinant strain highly producing fibrinogen and a production method thereof, which can stably supply safe fibrinogen free of a risk of contamination with infectious agents in a sufficient production amount, as well as a production method of a recombinant fibrinogen by using the recombinant strain highly producing fibrinogen of the present invention.

Means of Solving the Problems

The present inventors have conducted intensive studies in view of the above-mentioned object and found that not only degradation of fibrinogen can be strongly suppressed even in the later stage of culture when degradation of fibrinogen generally proceeds in animal cells, by coexpression of fibrinogen and α2PI and/or PAI-2, but also the production amount of fibrinogen can be increased independent of the suppressive effect on degradation of fibrinogen, and a synergistic effect thereof can strikingly increase the production amount of recombinant fibrinogen, which resulted in the completion of the present invention.

That is, the present invention relates to the following.

[1] A recombinant strain highly producing fibrinogen, which is an animal cell strain coexpressing fibrinogen and α2PI and/or PAI-2.

[2] The recombinant strain highly producing fibrinogen of the above-mentioned [1], wherein the fibrinogen and α2PI and/or PAI-2 are human fibrinogen and human α2PI and/or PAI-2.

[3] The recombinant strain highly producing fibrinogen of the above-mentioned [1] or [2], wherein the animal cell strain is CHO cell.

[4] A production method of a recombinant strain highly producing fibrinogen, comprising introducing genes encoding Aα chain, Bβ chain and γ chain of fibrinogen, and gene(s) encoding α2PI and/or PAI-2 into an animal cell, and coexpressing the fibrinogen and α2PI and/or PAI-2 in the animal cell.

[5] The method of the above-mentioned [4], comprising expressing fibrinogen in the animal cell by using a single expression vector comprising all of genes encoding Aα chain, Bβ chain and γ chain of fibrinogen.

[6] The method of the above-mentioned [4] or [5], comprising expressing α2PI and PAI-2 in the animal cell by using a single expression vector comprising a gene encoding α2PI and a gene encoding PAI-2.

[7] The method of any of the above-mentioned [4]-[6], wherein the genes encoding Aα chain, Bβ chain and γ chain of fibrinogen and the gene(s) encoding α2PI and/or PAI-2 are each a human gene.

[8] The method of any of the above-mentioned [4]-[7], wherein the animal cell is a CHO cell.

[9] A production method of a recombinant fibrinogen, comprising culturing the recombinant strain highly producing fibrinogen of any of the above-mentioned [1]-[3] or a recombinant strain highly producing fibrinogen, which is obtained by the method of any of the above-mentioned [4]-[8], in a medium, and recovering fibrinogen from the obtained culture.

Effect of the Invention

The recombinant strain highly producing fibrinogen of the present invention that strongly suppresses degradation of fibrinogen even in the later stage of culture when degradation of fibrinogen generally proceeds can not only increase the residual ratio of Aα chain by not less than about 2.5-fold compared to, for example, expression of fibrinogen alone, but also can increase the production amount of fibrinogen, independent of the suppressive effect on degradation of fibrinogen. As a result of the synergistic effect thereof, the production amount of fibrinogen is not less than about 4-fold that of a cell strain expressing fibrinogen alone. Therefore, using the recombinant strain highly producing fibrinogen of the present invention, a recombinant fibrinogen can be produced in a large amount, a recombinant fibrinogen can be formulated at a practical level, and stable supply of fibrinogen to the market can be secured.

Furthermore, since fibrinogen obtained by the recombinant strain highly producing fibrinogen of the present invention is produced by a gene recombination technique, the risk of contamination with infectious agents, which is a problem specific to a preparation derived from blood, can be eliminated completely, and sufficient safety can be secured.

Consequently, fibrinogen in an amount sufficient for the treatment can be used safely and securely for a long term.

BRIEF DESCRIPTION OF THE DRAWINGS

FIG. 9A shows the stained images. The stained gel was scanned by a densitometer (manufactured by Bio-Rad, Calibrated Densitometer GS-800), and variation in the fibrinogen Aα chain is shown by numerical values in FIG. 9B. pFbg shows fibrinogen (manufactured by CALBIOCHEM, 341576) derived from plasma. The relative value of the ratio of Aα chain to γ chain in each culture sample when the ratio of Aα chain to γ chain of pFbg is 100% is shown as the Aα chain residual ratio.

FIG. 10A shows the stained images. The stained gel was scanned by a densitometer (manufactured by Bio-Rad, Calibrated Densitometer GS-800), and variation in the fibrinogen Aα chain is shown by numerical values in FIG. 10B. Using attached software "Quantity One", band volume (band concentration×area) was measured. pFbg shows fibrinogen (manufactured by CALBIOCHEM, 341576) derived from plasma. The relative value of the ratio of Aα chain to γ chain in each culture sample when the ratio of Aα chain to γ chain of pFbg is 100% is shown as the Aα chain residual ratio.

DESCRIPTION OF EMBODIMENTS

Figure 1:
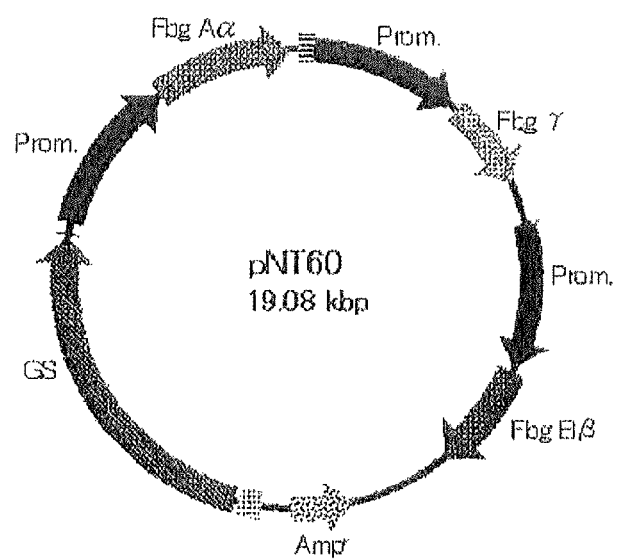
FIG. 1 shows fibrinogen expression vector pNT60.

In one embodiment, the present invention provides a recombinant strain highly producing fibrinogen, which is an animal cell strain coexpressing fibrinogen and α2PI and/or PAI-2.

In the present specification, a "strain" means a cell used interchangeably with a "cell strain", and grown or maintained in vitro.

In the present specification, a "(co)expressing animal cell strain" encompasses not only a state in which a gene encoding the object protein is introduced into an animal cell and expressed therein, but also a state in which said gene is integrated with the genome of the animal cell and constitutively expressing the object protein.

In the present specification, a "gene" may be either of DNA or RNA, DNA includes at least genomic DNA, cDNA, and RNA includes mRNA, synthetic RNA and the like. In the present specification, a "gene" may be a nucleic acid fragment having a base sequence free of an initiation codon and a stop codon, or optionally containing a signal sequence, an untranslated region (UTR) sequence and the like. In a preferable embodiment, the "gene" is cDNA.

In the present specification, an "animal cell strain coexpressing fibrinogen and α2PI and/or PAI-2" means an animal cell strain obtained by introducing genes encoding Aα chain, Bβ chain and γ chain of fibrinogen and gene(s) encoding α2PI and/or PAI-2 into an animal cell.

Therefore, in another embodiment, the present invention provides a production method of a recombinant strain highly producing fibrinogen, comprising introducing genes encoding Aα chain, Bβ chain and γ chain of fibrinogen and gene(s) encoding α2PI and/or PAI-2 into an animal cell, and coexpressing fibrinogen and α2PI and/or PAI-2 in the animal cell.

As genes encoding Aα chain, Bβ chain and γ chain of fibrinogen, which are to be used in the present invention, not only genes encoding a full-length wild-type fibrinogen chain, but also, for example, genes encoding any form of a fibrinogen chain can be used similarly, such as naturally-occurring genetic polymorphism, difference in glycosylation and phosphorylation, alternative splicing and the like, variants (e.g., αE chain, γ' chain and the like) due to a variant artificially induced by a method known per se, and the like, as long as the final expression product can constitute a functional fibrinogen. In addition, the animal species of the fibrinogen gene is not particularly limited, and a fibrinogen gene of any animal species can be used, which is preferably a gene encoding mammal, more preferably human fibrinogen.

In the present specification, a "functional fibrinogen" means a fibrinogen having an activity qualitatively the same as the physiological activity (e.g., blood's ability to clot and the like) of a wild-type fibrinogen, and the quantitative factors such as the level of activity, molecular weight and the like may be different.

As gene(s) encoding α2PI and/or PAI-2 to be used in the present invention, not only gene(s) encoding the full length wild-type α2PI and/or PAI-2, but also, for example, gene(s) encoding any form of α2PI and/or PAI-2 such as naturally-occurring variant, artificially induced variant and the like, can be used similarly, as long as an expression product thereof has an activity substantially qualitatively the same as that of wild-type α2PI and/or PAI-2. Also, the animal species of the α2PI and/or PAI-2 gene(s) are not particularly limited, and α2PI and/or PAI-2 gene(s) of any animal species can be used, which is preferably a gene encoding mammal, more preferably human α2PI and/or PAI-2.

In the present specification, having "an activity substantially qualitatively the same as that of wild-type α2PI and/or PAI-2" means that the activity is qualitatively the same as the physiological activity of wild-type α2PI and/or PAI-2 (e.g., plasmin inhibitory activity of α2PI, plasminogen activator inhibitory activity of PAI-2 and the like), where the quantitative factors such as the level of activity, molecular weight and the like may be different.

In a preferable embodiment, genes encoding Aα chain, Bβ chain and γ chain of fibrinogen and gene(s) encoding α2PI and/or PAI-2 are each a human gene.

The genes encoding Aα chain, Bβ chain and γ chain of fibrinogen and the gene(s) encoding α2PI and/or PAI-2 can be obtained by a method known per se. For example, it can be obtained by preparing primers for PCR by utilizing existing gene databases such as GENBANK and the like, and performing PCR using a full-length cDNA derived from a suitable cell or tissue expressing the object protein as a template. To facilitate subcloning to a vector, the primers for PCR may have a sequence of an appropriate restriction enzyme cleavage site on both ends, or optionally has a KOZAK sequence on the 5'-terminal to enhance expression efficiency. A full-length cDNA derived from a suitable cell or tissue may be obtained by a method known per se, for example, by purifying mRNA from the total RNA and converting same to cDNA, or a commercially available cDNA library may be utilized.

Alternatively, genes encoding Aα chain, Bβ chain and γ chain of fibrinogen and gene(s) encoding α2PI and/or PAI-2 can be purchased as a cDNA clone encoding only the desired gene sequence. For example, each cDNA of α2PI and PAI-2 is commercially available from Promega KK (manufactured by Promega, ORS09380 (α2PI) and ORS08641 (PAI-2)).

In the present invention, genes encoding Aα chain, Bp chain and γ chain of fibrinogen and gene(s) encoding α2PI and/or PAI-2 are introduced into an animal cell by using an expression vector. An expression vector using animal cell as a host is not particularly limited, and an expression vector known per se such as plasmid vector, virus vector and the like can be appropriately selected according to the object.

A promoter to be contained in a fibrinogen expression vector is not particularly limited as long as it efficiently functions in a host animal cell to be used, and finally affords a functional fibrinogen. For example, SV40 promoter, cytomegalovirus (CMV) promoter, RSV promoter, β actin promoter and the like can be mentioned. It is also possible to combine a promoter with a suitable enhancer A selective marker gene optionally contained in a fibrinogen expression vector is not particularly limited, and a to selective marker gene known per se such as neomycin resistance gene, puromycin resistance gene, hygromycin resistance gene, dihydrofolate reductase (dhfr) gene, glutamine synthase (GS) gene and the like can be appropriately selected according to the object.

Other vector constituent element (e.g., terminator and the like) optionally contained in a fibrinogen expression vector is not particularly limited, and one known per se can be utilized as appropriate.

In one embodiment, the fibrinogen expression vector of the present invention is a single expression vector comprising all of genes encoding Aα chain, Bβ chain and γ chain of fibrinogen. In another embodiment, the fibrinogen expression vector of the present invention is composed of an expression vector having two of genes encoding Aα chain, Bβ chain and γ chain of fibrinogen (e.g., Aα chain and γ chain, Bβ chain and γ chain and the like) and an expression vector having the remaining one. In another embodiment, the fibrinogen expression vector of the present invention is composed of 3 expression vectors each containing genes encoding Aα chain, Bβ chain and γ chain of fibrinogen. The constitution ratio of genes encoding Aα chain, Bβ chain, γ chain of fibrinogen is not particularly limited, and, for example, 1:1:1-6 and the like, can be appropriately selected according to the object. When fibrinogen is expressed using two or more expression vectors, respective expression vectors may be simultaneously introduced into an animal cell, or sequentially introduced at different times by using, for example, a different selective marker, where the order of introduction is not particularly limited. In a preferable embodiment, the fibrinogen expression vector of the present invention is a single expression vector containing all genes encoding Aα chain, Bβ chain, γ chain of fibrinogen at a constitution ratio of 1:1:1.

A preferable example of the single expression vector containing all genes encoding Aα chain, Bβ chain, γ chain of fibrinogen is one having 3 expression cassettes in which each gene encoding Aα chain, Bβ chain and γ chain of fibrinogen is under regulation of different promoters. The promoters regulating expression of each gene may be the same or different, and the same promoter (e.g., CMV promoter) is preferably used. Examples thereof include, but are not limited to, pNT60 (expression vector having modified CMV promoter/GS gene) (see FIG. 1), wherein cDNA of Aα chain, Bβ chain and γ chain of fibrinogen is inserted into a vector obtained by ligation of the three expression units of expression vector pEE14.1 manufactured by Lonza, by a method known per se.

Alternatively, two or more of genes encoding Aα chain, Bβ chain and γ chain of fibrinogen may be under regulation of a single promoter. In this case, a sequence enabling polycistronic expression (e.g., IRES sequence, 2A sequence derived from foot-and-mouth disease virus and the like) is inserted between each gene under control of a single promoter.

A promoter contained in α2PI and/or PAI-2 expression vector is not particularly limited as long as it efficiently functions in a host animal cell to be used and, for example, SV40 promoter, cytomegalovirus (CMV) promoter, RSV promoter, β actin promoter and the like can be mentioned. Also, a promoter may be combined with a suitable enhancer.

The α2PI and/or PAI-2 expression vector optionally contained in a selective marker gene is not particularly limited, and a selective marker gene known per se such as neomycin resistance gene, puromycin resistance gene, hygromycin resistance gene, dihydrofolate reductase (dhfr) gene, glutamine synthase (GS) gene and the like can be appropriately selected according to the object.

Other vector constituting element (e.g., terminator and the like) optionally contained in the α2PI and/or PAI-2 expression vector is not particularly limited, and one known per se can be utilized as appropriate.

When α2PI and PAI-2 are co-expressed, the α2PI and PAI-2 expression vector of the present invention may be a single expression vector containing a gene encoding α2PI and a gene encoding PAI-2, or a combination of an expression vector containing a gene encoding α2PI and an expression vector containing a gene encoding PAI-2. When α2PI and PAI-2 are expressed by using two expression vectors, respective expression vectors may be simultaneously introduced into an animal cell, or sequentially introduced at different times by using, for example, a different selective marker, where the order of introduction is not particularly limited. When both α2PI and PAI-2 are expressed, a single expression vector containing a gene encoding α2PI and a gene encoding PAI-2 is preferably used.

A preferable example of a single expression vector containing a gene encoding α2PI and a gene encoding PAI-2 is one having 2 expression cassettes in which each gene encoding α2PI and PAI-2 is under regulation of different promoters. The promoters regulating expression of each gene may be the same or different, and the same promoter (e.g., CMV promoter) is preferably used. Examples thereof include, but are not limited to, α2PI/PAI-2/pcDNA3.3-modified (expression vector containing CMV promoter/neomycin resistance gene) (FIG. 4), which is obtained by ligation of the two expression units of expression vector pcDNA3.3-TOPO/lacZ manufactured by Invitrogen (K8300-01 manufactured by Invitrogen), and inserting cDNA of α2PI and PAI-2 by a method known per se, and α2PI/PAI-2/m-pEE (expression vector containing CMV promoter/puromycin resistance gene) (FIG. 6), which is obtained by ligation of the two expression units of expression vector pEE manufactured by Lonza (e.g., pEE16.4, pEE21.4 and the like) and inserting cDNA of α2PI and PAI-2 by a method known per se.

Alternatively, a gene encoding α2PI and a gene encoding PAI-2 may be under regulation of a single promoter. In this case, a sequence enabling polycistronic expression (e.g., IRES sequence, 2A sequence derived from foot-and-mouth disease virus and the like) is inserted between each gene under control of a single promoter.

The timing and order of introduction of an expression vector of genes encoding Aα chain, Bβ chain and γ chain of fibrinogen, and an expression vector of gene(s) encoding α2PI and/or PAI-2 are not particularly limited, and they may be simultaneously introduced into an animal cell, or sequentially introduced at different times by using, for example, a different selective marker, as long as fibrinogen and α2PI and/or PAI-2 can be coexpressed in the same cell.

A host animal cell used for introduction of an expression vector of fibrinogen and α2PI and/or PAI-2 is not particularly limited, and any animal cells such as Chinese hamster ovary (CHO) cell, mouse myeloma cell, BHK cell, HEK293 cell, HeLa cell, COS cell and the like can be utilized and can be appropriately selected according to the object. In a preferable embodiment, the animal cell in the present invention is a CHO cell. In another preferable embodiment, the animal cell of the present invention is a floating cultured cell. In a still another preferable embodiment, the animal cell of the present invention is acclimated to a serum-free medium.

As a transformation method of a host animal cell, a method known per se may be used. Examples thereof include, but are not limited to, calcium phosphate method, DEAE dextran method, a method using a liposome such as lipofectin, lipofectamine and the like, protoplast-PEG method, electroporation method and the like.

When an expression vector containing a selective marker gene is introduced into an animal cell, a transformed cell can be selected by a selection method known per se. For example, a transformed cell can be easily selected by adding an addition substance for selection (e.g., G-418 when the selective marker gene is neomycin resistance gene, methotrexate when it is a dhfr gene, puromycin when it is a puromycin resistance gene and the like) to a serum-free medium such as CD-CHO medium (manufactured by GIBCO) and the like, a serum medium such as D-MEM/Ham's F-12 medium (manufactured by Wako Pure Chemical Industries, Ltd.) added with 10% fetal bovine serum (FCS) and the like, and culturing same.

After selection of a transformed cell, the detection or measurement of the expression level of the object protein may be performed by utilizing, for example, radioimmunoassay (RIA), enzyme antibody method (ELISA), Western blot method (WB) and the like. When the object protein has some activity, the activity can also be directly measured.

In one embodiment, the present invention provide a production method of a recombinant fibrinogen, comprising culturing a recombinant strain highly producing fibrinogen of the present invention in a medium, and recovering fibrinogen from the obtained culture.

The recombinant strain highly producing fibrinogen of the present invention not only strongly suppresses degradation of fibrinogen even in the later stage of culture when cell density is high and degradation of fibrinogen generally proceeds markedly, but also can increase the production amount of fibrinogen, independent of the suppressive effect on degradation of fibrinogen. As a result of the synergistic effect thereof, the recombinant fibrinogen can be produced in a large amount. Therefore, a culture method known per se such as a general culture method (e.g., Batch culture method and the like), as well as a high density cell culture method, for example, Fed-Batch culture method, perfusion culture method and the like can be used without limitation for the recombinant strain highly producing fibrinogen of the present invention. In addition, other culture conditions, for example, pH of medium, culture temperature and the like are not particularly limited, and culture conditions suitable for the growth of animal cells and the production of fibrinogen and α2PI and/or PAI-2 can be appropriately adopted. Furthermore, the medium is not particularly limited, and it may be a serum containing medium or serum-free medium. In a preferable embodiment, a serum-free medium is used since, when a serum-free medium is used for culture, stable production of protein is afforded with reproducibility irrespective of the lot difference of sera, the product can be purified easily since a serum-derived protein component is not contained and the like.

A method of culturing a recombinant strain highly producing fibrinogen of the present invention in a medium, and recovering fibrinogen from the obtained culture is not particularly limited as long as fibrinogen can be recovered from the culture and, for example, a method known per se such as ethanol fractionation, glycine fractionation, ion exchange chromatography, affinity chromatography, ammonium sulfate precipitation and the like can be mentioned.

The recombinant strain highly producing fibrinogen of the present invention can stably supply safe fibrinogen free of a risk of contamination with infectious agents in a sufficient production amount. Therefore, in one embodiment, the recombinant strain highly producing fibrinogen of the present invention is used for the production of fibrinogen for use in a replacement therapy of congenital and acquired fibrinogen deficiency and the like. In another embodiment, the recombinant strain highly producing fibrinogen of the present invention is used for the production of fibrinogen for use in adhesion and closing of tissues during surgery. In another embodiment, the recombinant strain highly producing fibrinogen of the present invention is used for the production of fibrinogen for use as a fibrin sealant.

EXAMPLES

The present invention is explained in more detail in the following by referring to Examples, which are mere exemplifications and do not at all limit the scope of the present invention.

Example 1: Establishment of Fibrinogen Expressing Cell Strain cDNAs of Aα chain, Bβ chain, γ chain of fibrinogen, which were amplified from human liver-derived cDNA library (manufactured by Takara Bio Inc., 9505) by using the PCR primer shown in the following Table 1, were inserted into a vector obtained by ligation of the three expression units of expression vector pEE14.1 manufactured by Lonza to construct fibrinogen expression vector pNT60 (expression vector having modified CMV promoter/GS gene) (FIG. 1). pNT60 was introduced into CHO-K1 cell established by Lonza, cultured in an animal component-free medium (EX-cell302GS medium described in Table 3), and cells expressing fibrinogen Aα chain, Bβ chain and γ chain were selected. Then, a transformed cell having high fibrinogen producibility was further selected to establish fibrinogen expressing cell strain T233, and the reproducibility of fibrinogen production was confirmed.

TABLE 1

Table 1: PCR primer

| primer name | length (bp) | sequence (3'-5') |
| --- | --- | --- |
| LOAα-F (SEQ ID NO: 1) | 30 | GG<u>AAGCTT</u>GCCACC<u>ATG</u>TTTTCCATGAGGA HindIII Kozak Met |
| LOAα-R (SEQ ID NO: 2) | 30 | GG<u>CCCGGG</u>CTAGACAGGGCGAGATTTAGCA Sma I * |
| LOBβ-F (SEQ ID NO: 3) | 30 | GG<u>AAGCTT</u>GCCACC<u>ATG</u>AAACATCTATTAT HindIII Kozak Met |
| LOBβ-R (SEQ ID NO: 4) | 30 | GGG<u>AATTC</u>CTATTGCTGTGGGAAGAAGGGC EcoR I * |
| LOγ-F (SEQ ID NO: 5) | 30 | GG<u>AAGCTT</u>GCCACC<u>ATG</u>AGTTGGTCCTTGC HindIII Kozak Met |
| LOγ-R (SEQ ID NO: 6) | 30 | GGG<u>AATTC</u>TTAAACGTCTCCAGCCTGTTTG EcoR I * |

* termination codon

The fibrinogen expressing cell strain T233 obtained by the above-mentioned method was cultured in a large scale by 2 L jar culture to produce 1.8 g/L of recombinant fibrinogen and a degradation product thereof in total, wherein not less than a half thereof was a degradation product. Then, the degradation product was removed, and a swine skin adhesion test was performed using the purified recombinant fibrinogen. As a result, recombinant fibrinogen showed an adhesion effect equivalent to that of plasma-derived fibrinogen. From the foregoing results, it was confirmed that fibrinogen expressing cell strain T233 can stably express a fibrinogen having a physiological activity equivalent to that of a natural type.

Example 2: Construction of α2PI/PAI-2 Expression Vector (α2PI/PAI-2/pcDNA3.3-Modified)-1)

For construction of a vector to be used for expression of α2PI and PAI-2 in an animal cell, ligation of the two expression units of an expression vector pcDNA3.3-TOPO/lacZ (manufactured by Invitrogen, K8300-01) for animal cell was performed.

Figure 2:
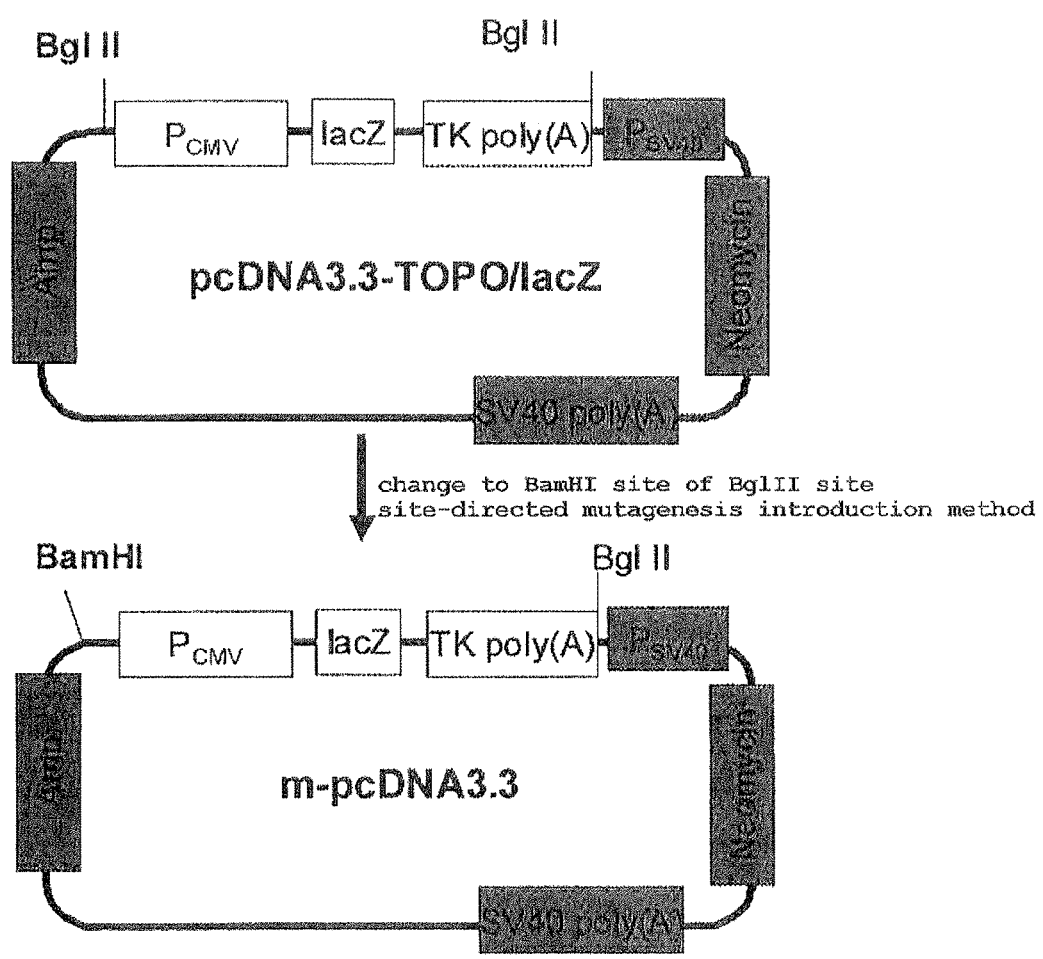
FIG. 2 shows site-specific mutagenesis of expression unit of pcDNA3.3-TOPO/lacZ.

To be specific, using pcDNA3.3-TOPO/lacZ and two kinds of primers (BamHI-Fw:CCCTATGGTC-GACTCTCAGTACAATCTG (SEQ ID NO:7) and BamHI-Rv:GATCCGTCGACGTCAGGTGGCACTTTTC (SEQ ID NO:8)), BglII was changed to BamHI by a site-specific mutagenesis introduction method (KOD-Plus-Mutagenesis Kit, manufactured by TOYOBO CO., LTD., SMK-101) to give a modified vector m-pcDNA3.3 (FIG. 2).

Figure 3:
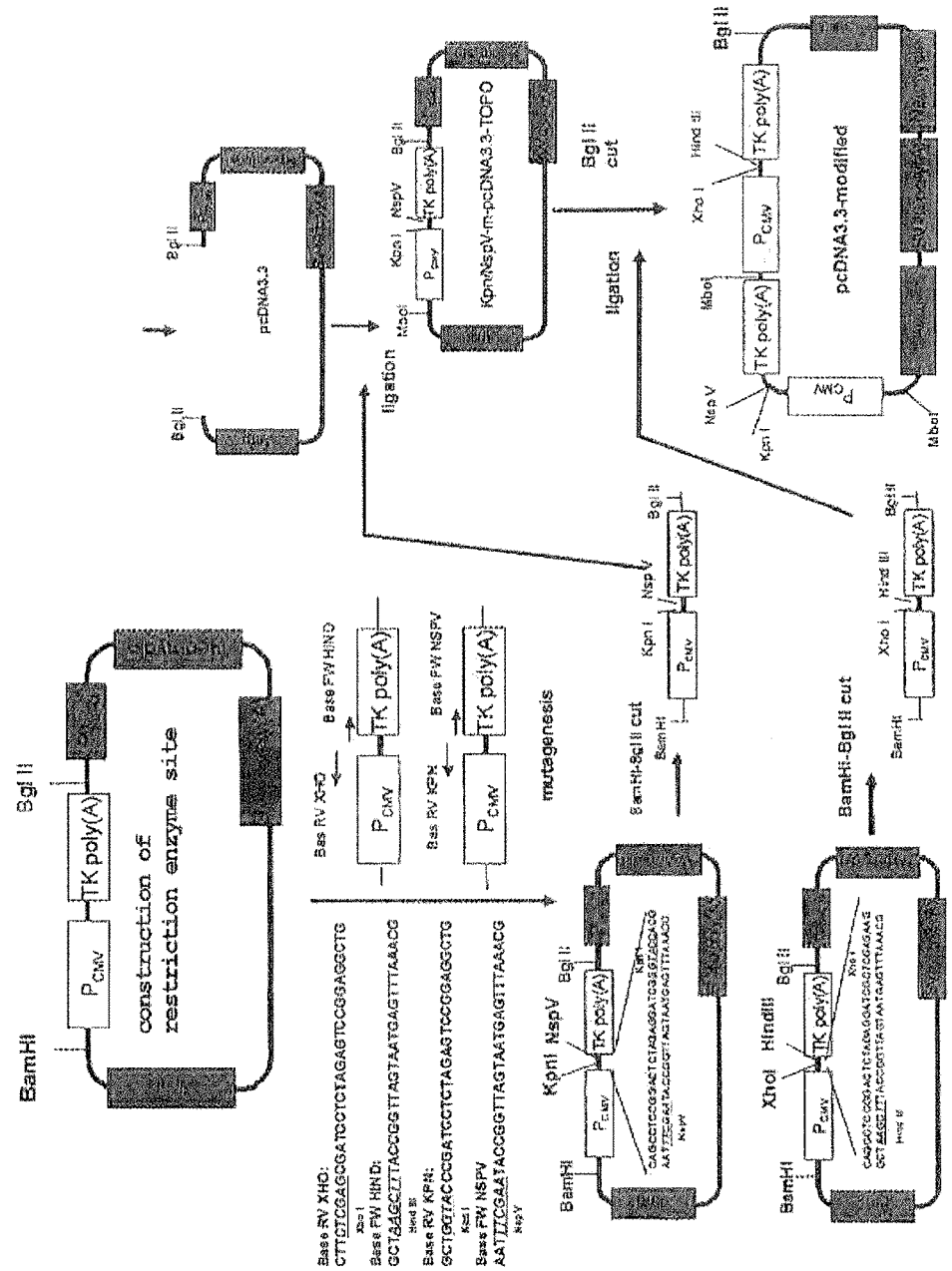
FIG. 3 shows a construction method of pcDNA3.3-modified. wherein the primer sequences are as follows: Base RV XHO (XhoI) is SEQ ID NO: 11; Base FW HIND (HindIII) is SEQ ID NO: 12; Base RV KPN (KpnI) is SEQ ID NO: 9; and Base FW NSPV (NspV) is SEQ ID NO: 10.

To insert cDNA of α2PI or PAI-2 between CMV promoter and TK poly(A) of m-pcDNA3.3, a restriction enzyme recognition sequence was added by a site-specific mutagenesis introduction method (KOD-Plus-Mutagenesis Kit, manufactured by TOYOBO CO., LTD., SMK-101) by PCR. KpnI recognition sequence and NspV recognition sequence were added to the downstream of the CMV promoter of m-pcDNA3.3 for α2PI by using a specific primer (Base RV KPN: GCTGGTACCCGATCCTCTAGAGTCCGGAG-GCTG (SEQ ID NO:9) and Base FW NSPV: AATTTC-GAATACCGGTTAGTAATGAGTTTAAACG (SEQ ID NO:10)). XhoI recognition sequence and HindIII recognition sequence were introduced into the downstream of the CMV promoter of m-pcDNA3.3 for PAI-2 by using a specific primer (Base RV XHO: CTTCTCGAGCGATC- CTCTAGAGTCCGGAGGCTG (SEQ ID NO:11) and Base FW HIND: GCTAAGCTTTACCGGTTAGTAATGAGTT-TAAACG (SEQ ID NO:12)). The constructed expression vectors were KpnI/NspV-m-pcDNA3.3 and XhoI/HindIII-m-pcDNA3.3, respectively. Then, KpnI/NspV-m-pcDNA3.3 was digested with BglII (manufactured by Takara Bio Inc., 1021A) and BamHI (manufactured by Takara Bio Inc., 1010A), and the fragment was inserted into pcDNA3.3-TOPO (manufactured by Invitrogen) digested in advance with BglII. The thus-produced vector was KpnI/NspV-m-pcDNA3.3-TOPO. Then, XhoI/HindIII-m-pcDNA3.3 was treated with BglII and BamHI, and the fragment was inserted into KpnI/NspV-m-pcDNA3.3-TOPO digested in advance with BglII to give pcDNA3.3-modified (FIG. 3).

Using cDNA of PAI-2 (manufactured by Promega, ORS08641) as a template, and specific primers (PAI-2 F XHO: AACCTCGAGGCCGCCACCATGGAGGATCTTT-GTGTGGCAAAC (SEQ ID NO:13) and PAI-2 RV HIND: GGGAAGCTTAGGGTGAGGAAAATCTGCCG (SEQ ID NO:14)), an open reading frame (ORF) portion of PAI-2 was amplified by PCR (KOD-plus, manufactured by TOYOBO CO., LTD., KOD-201), and Kozak sequence, XhoI recognition sequence and HindIII recognition sequence were added. The amplified fragment and pcDNA3.3-modified were digested with XhoI (manufactured by Takara Bio Inc., 1094A) and HindIII (manufactured by Takara Bio Inc., 1060A), and the fragment was inserted into XhoI-HindIII of pcDNA3.3-modified. The vector produced thereby was PAI-2/pcDNA3.3-modified.

Figure 4:
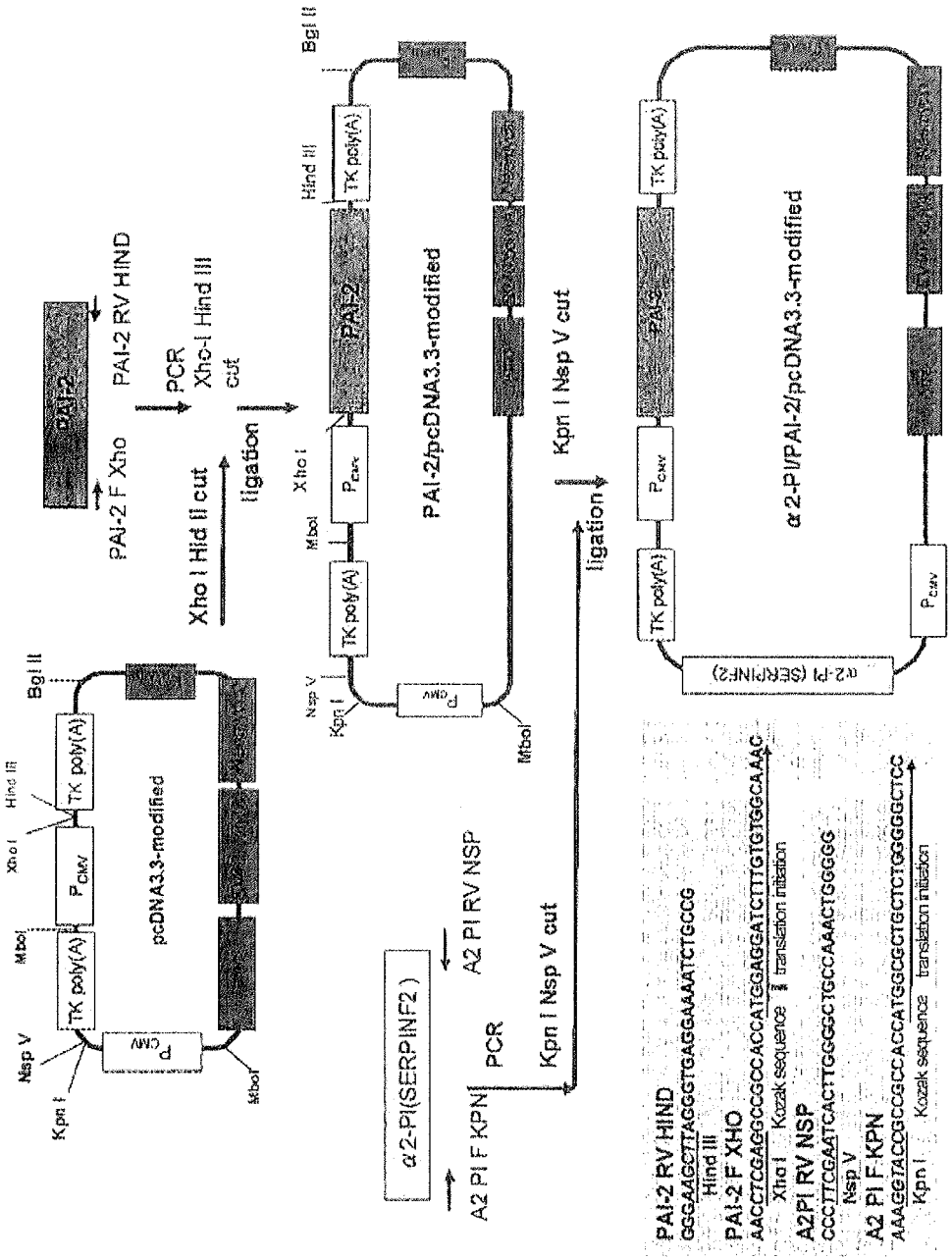
FIG. 4 shows a construction method of a2PI/PAI-2/pcDNA3.3-modified, wherein the primer sequences are as follows: PAI-2 RV HIND (HindIII) is SEQ ID NO: 14; PAI-2 F XHO (XhoI Kozak sequence) is SEQ ID NO: 13; A2PI RV NSP (NspV) is SEQ ID NO: 16; and A2 PI F KPN (KpnI Kozak sequence) is SEQ ID NO: 15.

Using cDNA of α2PI (manufactured by Promega, ORS09380) as a template, and specific primers (α2PI F KPN: AAAGGTACCGCCGCCACCATGGCGCT-GCTCTGGGGGCTCC (SEQ ID NO:15) and α2PI RV NSP: CCCTTCGAATCACTTGGGGCTGC-CAAACTGGGGG (SEQ ID NO:16)), the ORF portion of α2PI was amplified by PCR, and Kozak sequence, KpnI recognition sequence and NspV recognition sequence were added. The amplified fragment and PAI-2/pcDNA3.3-modified were digested with KpnI (manufactured by Takara Bio Inc., 1068A) and NspV (manufactured by Takara Bio Inc., 1225A), and the fragment was ligated with PAI-2/pcDNA3.3-modified. The thus-constructed vector was α2PI/PAI-2/pcDNA3.3-modified (FIG. 4).

The constructed α2PI/PAI-2/pcDNA3.3-modified is mounted with two expression cassettes regulated by the CMV promoter, respectively inserted with ORF of α2PI and ORF of PAI-2. Furthermore, a neomycin resistance gene used as a selective marker in animal cells is mounted, which is expressed under regulation of the SV40 promoter. Therefore, a constantly expressing cell strain can be constructed by selection using G418.

Example 3: Construction of α2PI/PAI-2 Expression Vector (α2PI/PAI-2/m-pEE)-2)

For construction of a vector to be used for expression of α2PI and PAI-2 in an animal cell, ligation of the two expression units of an expression vector pEE (manufactured by Lonza) for animal cell was performed.

Figure 5:
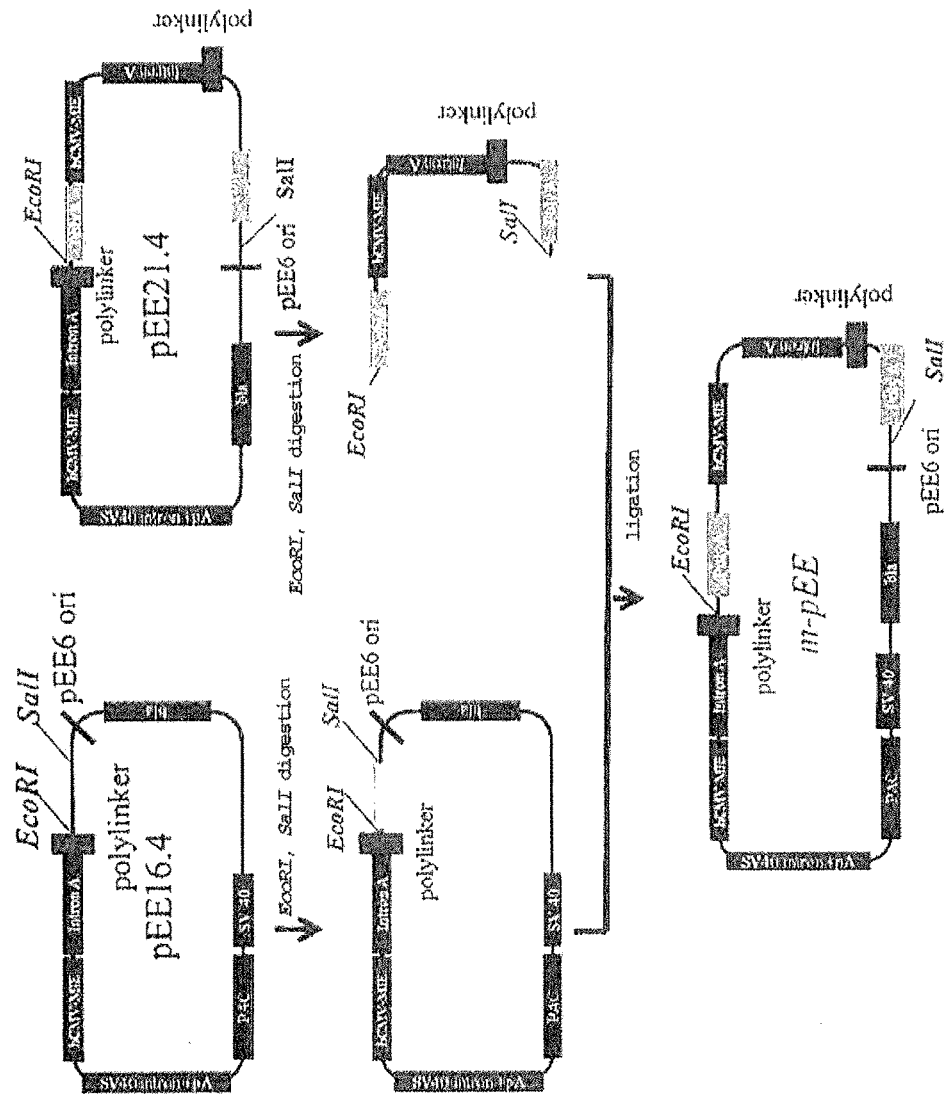
FIG. 5 shows a construction method of m-pEE.

To be specific, the vector was modified by using pEE16.4 and pEE21.4 manufactured by Lonza. pEE21.4 was digested with restriction enzymes EcoRI and SalI, and 2.9 kb DNA fragment was isolated. pEE16.4 was digested with restriction enzymes EcoRI and SalI to isolate a 6.1 kb DNA fragment, and the above-mentioned DNA fragment derived from pEE21.4 was inserted therein. The modified vector was m-pEE (FIG. 5).

To insert cDNA of α2PI or PAI-2 between intron A and poly(A) of m-pEE, the ORF portion was first amplified by PCR (KOD-plus, manufactured by TOYOBO CO., LTD., KOD-201) using cDNA of PAI-2 (manufactured by Promega, ORS08641) as a template and specific primers (PAI-2 F hind: AACAAGCTTGCCGCCACCATGGAG-GATCTTTGTGTGGCAAAC (SEQ ID NO:19) and PAI-2 RV nsp: GGGTTCGAATTAGGGTGAGGAAAATCT-GCCG (SEQ ID NO:20)), and Kozak sequence, HindIII recognition sequence and NspV recognition sequence were added. The amplified fragment was digested with HindIII (manufactured by Takara Bio Inc., 1060A) and BspT104I (manufactured by Takara Bio Inc., 1225A) and inserted between HindIII-NspV of m-pEE. The vector produced thereby was PAI-2/m-pEE.

Figure 6:
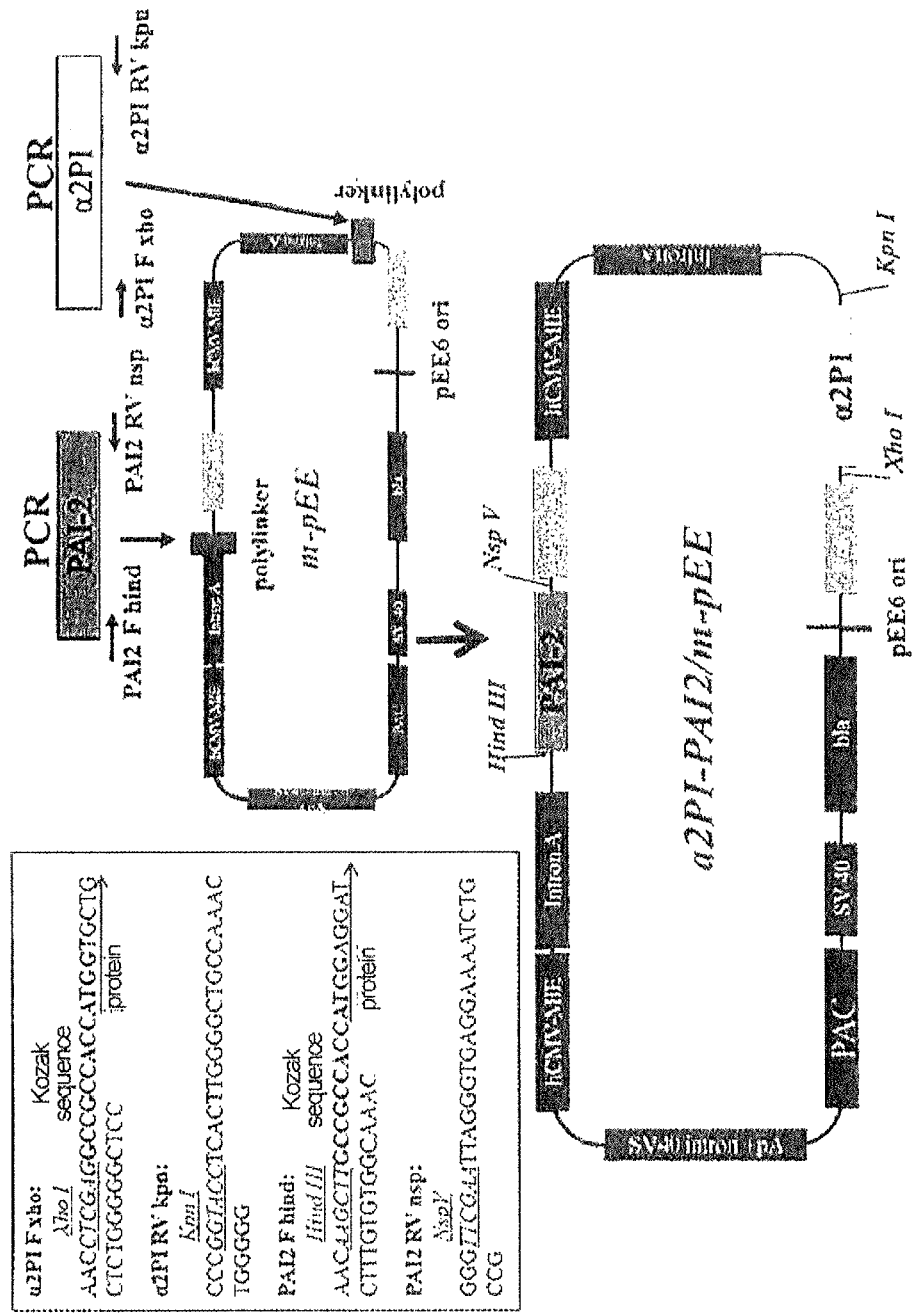
FIG. 6 shows a construction method of a2PI/PAI-2/m-pEE, wherein the primer sequences are as follows: α2PI F xho (XhoI Kozak sequence) is SEQ ID NO: 17; α2PI RV kpn (KpnI) is SEQ ID NO: 18; PAI2 F hind (HindIII Kozak sequence) is SEQ ID NO: 19; and PAI2 RV nsp (NspV) is SEQ ID NO: 20.

Then, the ORF portion was amplified by PCR using cDNA of α2PI (manufactured by Promega, ORS09380) as a template and specific primers (α2PI F xho: AACCTCGAG-GCCGCCACCATGGTGCTGCTCTGGGGGCTCC (SEQ ID NO:17) and α2PI RV kpn: CCCGGTACCTCACT-TGGGGCTGCCAAACTGGGGG (SEQ ID NO:18)), and Kozak sequence, XhoI recognition sequence and KpnI recognition sequence were added. The amplified fragment was digested with XhoI (manufactured by Takara Bio Inc., 1094A) and KpnI (manufactured by Takara Bio Inc., 1068A), and ligated to PAI-2/m-pEE. The thus-constructed vector was α2PI/PAI-2/m-pEE (FIG. 6). The following Table 2 shows the sequences of PCR primers used in this Example.

TABLE 2

Table 2: PCR primer

| primer name | length(bp) | sequence (3'-5') |
|---|---|---|
| a2PI F xho (SEQ ID NO: 17) | 40 | AAC<u>CTCGAG</u><u>GCCGCCACC</u><u>ATG</u>GTGCTGCTCTGGGGGCTCC<br>   Xho I   Kozak   Met |
| a2PI RV kpn (SEQ ID NO: 18) | 34 | CCC<u>GGTACCT</u>CACTTGGGGCTGCCAAACTGGGGG<br>   Kpn I   * |
| PAI2 F hind (SEQ ID NO: 19) | 42 | AAC<u>AAGCTT</u><u>GCCGCCACC</u><u>ATG</u>GAGGATCTTTGTGTGGCAAAC<br>   HindIII   Kozak   Met |
| PAI2 RV Nsp (SEQ ID NO: 20) | 31 | GGG<u>TTCGAAT</u>TAGGGTGAGGAAAATCTGCCG<br>   Nsp V   * |

* termination codon

The constructed α2PI/PAI-2/m-pEE is mounted with two expression cassettes regulated by the CMV promoter, respectively inserted with ORF of α2PI and ORF of PAI-2. Furthermore, a puromycin resistance gene used as a selective marker in animal cells is mounted, which is expressed under regulation of the SV40 promoter. Therefore, a constantly expressing cell strain can be constructed by selection using puromycin.

Example 4: Establishment of Fibrinogen and α2PI and PAI-2 Coexpressing Cell Strain Fibrinogen expressing cell strain T233 obtained in Example 1 was suspended in 10% FCS (manufactured by Hyclone, SH3088)-containing D-MEM/Ham's F-12 medium (manufactured by Wako Pure Chemical Industries, Ltd., 048-29785) at a cell density of $0.5$-$2.5\times10^5$ cells/mL, and seeded in a 6-well plate at 2 mL per well. Then, the cells were incubated at 37° C., 5% $CO_2$ for about 16 hr. After exchanging with a fresh medium (1 mL), α2PI and PAI-2 genes were introduced using Lipofectamin 2000 (manufactured by Invitrogen, 11668). To be specific, α2PI/PAI-2/pcDNA3.3-modified (4.0 μg) or α2PI/PAI-2/m-pEE (4.0 μg) was linearized by digestion with ScaI (manufactured by Takara Bio Inc., 10844) and dissolved in 80 μL of Opti-MEM (manufactured by Invitrogen, 31985-070) to give SOLUTION A and 4 μL of Lipofectamin 2000 was added to 80 μL of Opti-MEM to give SOLUTION B and they were each stood at room temperature for 5 min. SOLUTION A and SOLUTION B were mixed and the mixture was stood at room temperature for 20 min. The mixture was added to the well at 160 μL per well and incubated at 37° C., 5% $CO_2$ for 16-24 hr. α2PI and PAI-2 genes were introduced into fibrinogen expressing cell strain T233, which was washed with PBS(-) and treated with trypsin (manufactured by Invitrogen, 12604), and the cells were recovered.

As for fibrinogen expressing cell strain T233 introduced with α2PI and PAI-2 genes by using α2PI/PAI-2/pcDNA3.3-modified, the cells were suspended in 10% FCS-containing D-MEM/Ham's F-12 medium added with 800 μg/mL of G418 (manufactured by CALBIOCHEM, 345812), and seeded in a 96 well plate at a cell density of $1\times10^3$ cells/well. After culture for about 2 weeks (37° C., 5% $CO_2$), G418 resistance cell strain was selected (coexpressing cell strains α2PI/PAI-2/T233 #9 and #15).

As for fibrinogen expressing cell strain T233 introduced with α2PI and PAI-2 genes by using α2PI/PAI-2/m-pEE, the cells were suspended in 10% FCS-containing D-MEM/Ham's F-12 medium added with 10 μg/mL of puromycin (manufactured by Invivogen, ant-pr-1), and seeded in a 96 well plate at a cell density of $1\times10^2$ cells/well, $1\times10^3$ cells/well, $1\times10^4$ cells/well. After culture for about 2 weeks (37° C., 5% $CO_2$), puromycin resistance cell strain was selected (coexpressing cell strains α2PI/PAI-2/T233 #8 and #68).

Example 5: Confirmation of Expression of α2PI, PAI-2 and Fibrinogen Aα, Bβ, γ Chains 1. Confirmation of Protein Expression of α2PI and PAI-2

Fibrinogen expressing cell strain T233 and coexpressing cell strains α2PI/PAI-2/T233 #9 and #15 were each suspended in Fed-Batch medium (Table 3) at a cell density of $1\times10^6$ cells/mL, 5 mL thereof was seeded in a 125 mL flask and cultured by shaking the flask for 10 days (37° C., 5% $CO_2$, 120-140 rpm). 10 μL of the culture supernatant was subjected to SDS-PAGE, and the gel after electrophoresis was transferred onto a nitrocellulose filter (manufactured by Invitrogen, IB301001) by using iBlot Gel Transfer Device (manufactured by Invitrogen, IB1001). The filter was blocked with a blocking buffer (3% skim milk (manufactured by Nacalai Tesque) containing TBS (20 mM Tris-HCl, 0.1 M NaCl, pH=8.0)) for 30 min. The anti-α2PI antibody (manufactured by Santa Cruz, SC-73658) or anti-PAI-2 antibody (manufactured by Santa Cruz, SC-25745) diluted 200-fold with the blocking buffer was added and the mixture was incubated at room temperature for 2 hr. The filter was washed 3 times with 0.02% (w/v) Tween 20-containing TBS for 10 min. Anti-mouse IgG[H+L] (mouse)-HRP complex (manufactured by Nacalai Tesque, 01803-44) 10,000-fold diluted with the blocking buffer was added to the anti-α2PI antibody-treated filter, and the anti-rabbit IgG[H+L] (goat)-HRP complex (manufactured by Nacalai Tesque, 01827-44) 10,000-fold diluted with the blocking buffer was added to the anti-PAI-2 antibody-treated filter, and they were each incubated at room temperature for 1 hr. The filters were washed 3 times with 0.02% (w/v) Tween20-containing TBS for 10 min, and the expression of α2PI and PAI-2 was detected using Super Signal West Dura Extended Duration Substrate (manufactured by Thermo, 34075).

Figure 7:
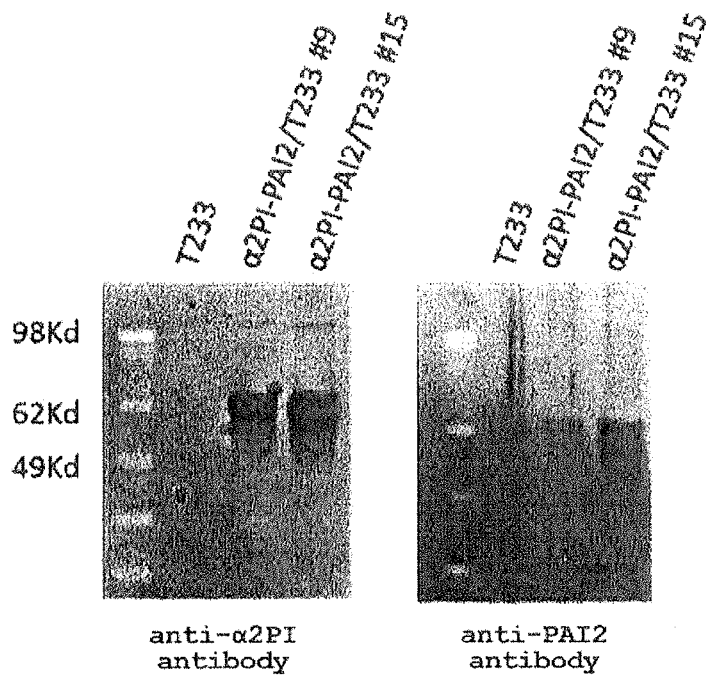
FIG. 7 shows Western blot confirming expression of a2PI and PAI-2 after culture of fibrinogen expressing cell strain T233, and coexpressing cell strains a2PI/PAI-2/T233 #9 and #15 for 10 days.

As a result, expression of transfected α2PI and PAI-2 was each confirmed in the culture supernatants of coexpressing cell strains α2PI/PAI-2/T233 #9 and #15 (FIG. 7). As for PAI-2, PAI-2 derived from the host animal cell (CHO cell) was also expressed in fibrinogen expressing cell strain T233, and an increase in the expression level by the introduction of PAI-2 gene was confirmed.

TABLE 3

Table 3: EX-cell 302GS (modified 60756, manufactured by Nichirei Biosciences Inc., 5542-40 L4475) medium composition (g/L)

| reagent | Batch medium | Fed-Batch medium |
| --- | --- | --- |
| EX-cell 302GS (modified 60756) | 12.84 | 12.84 |
| D-glucose | 2.92 | 2.92 |
| L-sodium glutamate | 1.04 | 1.04 |
| sodium chloride | 6.00 | — |
| phenol red | 0.0066 | 0.0066 |
| sodium hydrogen carbonate | 1.6 | — |
| L-tyrosine 2sodium | — | 1.2 |
| penicillin and streptomycin: 10,000 U/mL penicillin 10,000 μg/mL streptomycin | 1/100 amount | |
| 12.5 mM methionine sulfoximine (MSX) | 1/500 amount | |

The osmotic pressure of Fed-Batch medium was adjusted as with saline.

2. Confirmation of mRNA Expression of α2PI, PAI-2 and Fibrinogen Aα, Bβ, γ Chains Fibrinogen expressing cell strain T233, and coexpressing cell strain α2PI/PAI-2/T233 #15 established using α2PI/PAI-2/pcDNA3.3-modified, and coexpressing cell strains α2PI/PAI-2/T233 #8 and #68 established using α2PI/PAI-2/m-pEE were suspended in Batch medium (Table 3) at a cell density of $1\times10^6$ cells/mL, 125 mL thereof was seeded in a 20 mL flask and cultured by shaking the flask for 6 days (37° C., 5% $CO_2$, 120-140 rpm). The amount of mRNA in the cultured cells was measured by quantitative PCR, and expression of transgene was confirmed.

Extraction of RNA and reverse transcription reaction were performed as follows according to the attached protocol by using TaqMan (registered trade mark) Gene Expression Cells-to-CT™ kit (manufactured by Applied Biosystems, 4399002). The cells on day 6 of culture were washed with cold PBS(−) and cold PBS(−) was prepared at 2.0×10⁶ cells/mL. 5 μL of the cell suspension was placed in a microtube, and 50 μL of Lysis Solution containing 0.5 μL of DNaseI was added. The reaction mixture was pipetted, and incubated at room temperature for 5 min. Stop Solution (5 μL) was added, and the mixture was incubated at room temperature for 2 min, and the RNA extract was prepared. 40 μL of RT master MIX (2× RT Buffer 25 μL, 20×RT Enzyme MIX 2.5 μL, Nuclease-free water 12.5 μL) and 10 μL of RNA extract were mixed, and reverse transcription reaction (incubation at 37° C. for 30 min, and then at 95° C. for 5 min) was performed.

Quantitative PCR was performed using HRM real-time PCR analysis system (manufactured by Bio-Rad, 185-5196-J4CAM), and the amount of reversely transcribed DNA was measured. To be specific, it was performed as follows according to the attached protocol and using TaqMan Universal PCR Master Mix (manufactured by Applied Biosystems, 4304437) and TaqMan Primer & Probe Mix (×20) (Table 4). TaqMan Universal PCR Master Mix (10 μL), Primer & Probe Mix (1 μL), reverse transcription reaction mixture (2 μL), and sterilized distilled water (7 μL) were mixed. PCR reaction included a pre-treatment including incubation at 50° C. for 2 min, followed by incubation at 95° C. for 10 min, and 40 repeats of reaction at 95° C. for 15 sec, and 60° C. for 1 min.

TABLE 4

Table 4: Assay ID of TaqMan Assay (Primer & Probe Mix (x20))

| name | Assay ID |
| --- | --- |
| Fibrinogen alpha chain | Hs00241027 |
| Fibrinogen beta chain | Hs00905942 |
| Fibrinogen gamma chain | Hs00241037 |
| Serpin peptidase inhibitor, clade B (ovalbumin), member 2 | Hs01010736 |
| Serpin peptidase inhibitor, clade F (alpha-2 antiplasmin, pigment epitherium derived factor), member 2 | Hs00168686 |

Figure 8:
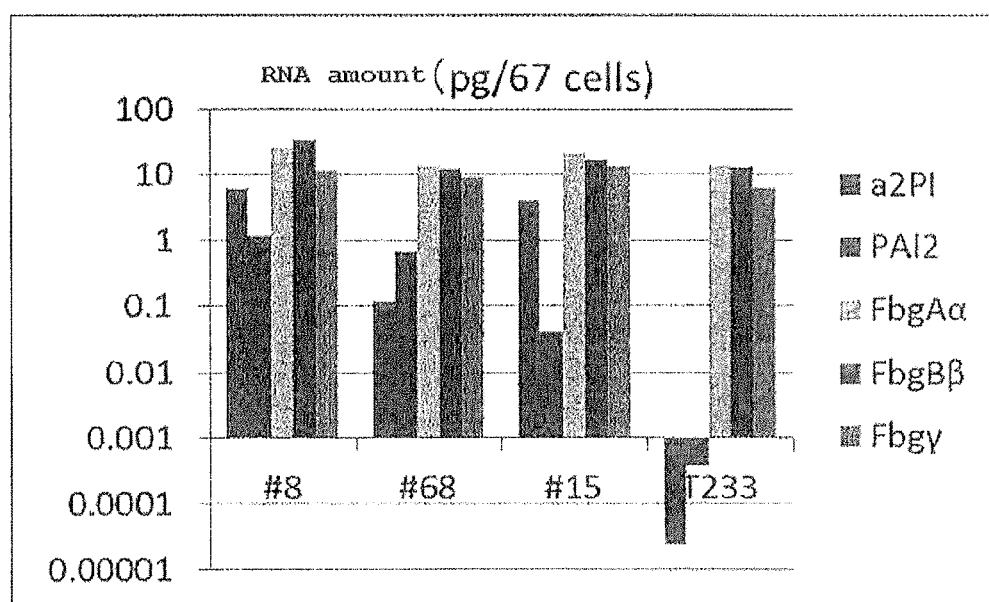
FIG. 8 shows the mode of mRNA expression by transgene in coexpressing cell strains α2PI/PAI-2/T233 #15, #8 and #68. 67 cells were used for one reaction. The fibrinogen mRNA expression level was calculated as an amount per pNT60 by using, as a control, a sample, wherein fibrinogen expression vector pNT60 was diluted in 4 stages from 100 pg/mL to 0.1 pg/mL by 10-fold dilution. Similarly, the expression level of α2PI and PAI-2 was calculated as an amount per expression vector α2PI/PAI-2/pcDNA3.3-modified (α2PI/PAI-2/T233 #15) or α2PI/PAI-2/m-pEE (α2PI/PAI-2/T233 #8 and #68). To afford values between respective cells, the value of each cell was calculated based on the GAPDH expression level in T233 cell as 1, and normalized by multiplying the value of each sample by the inverse number thereof.

As for the expression level of mRNA on day 6 of culture, the expression of α2PI and PAI-2 was not detected in the fibrinogen expressing cell strain T233 cell, whereas clear expression was detected in the coexpressing cell strains α2PI/PAI-2/T233 #15, #8 and #68, whereby it was clarified that introduced expression vector functioned (FIG. 8). In the coexpressing cell strains α2PI/PAI-2/T233 #8 and #68 established using α2PI/PAI-2/m-pEE, about 10 times higher PAI-2 mRNA level was detected as compared to the coexpressing cell strain α2PI/PAI-2/T233 #15 established using α2PI/PAI-2/pcDNA3.3-modified, and a difference in the expression level due to the vector was confirmed. As for the expression level of α2PI mRNA, the coexpressing cell strain α2PI/PAI-2/T233 #8 and the coexpressing cell strain α2PI/PAI-2/T233 #15 showed equivalent expression. However, the expression level was 1/10 in the coexpressing cell strain α2PI/PAI-2/T233 #68, thus showing a difference in the expression level between cell strains. On the other hand, as for fibrinogen, expression of Aα chain, Bβ chain and γ chain was confirmed in all cell strains. The expression level was not different between the fibrinogen expressing cell strain T233 and the coexpressing cell strains α2PI/PAI-2/T233 #15, #8 and #68 (FIG. 8).

Example 6: Suppression of Degradation of Fibrinogen Aα Chain in Culture

Generally, cultured cells grow in the order of lag phase, logarithmic growth phase, stationary phase, and death phase, where the number of cultured cells and the amount of recombinant protein production are correlated. Therefore, when a recombinant protein is produced, an extension of the period of stationary phase when the number of cultured cells reaches the peak, i.e., the later stage of culture, is considered to lead to an increase in the production amount of recombinant protein, and progress of degradation of fibrinogen in the later stage of culture when the cell density is high poses a fatal problem for the large scale production of fibrinogen. Therefore, whether degradation of fibrinogen can be suppressed under culture conditions of high cell density was examined.

Figure 9:
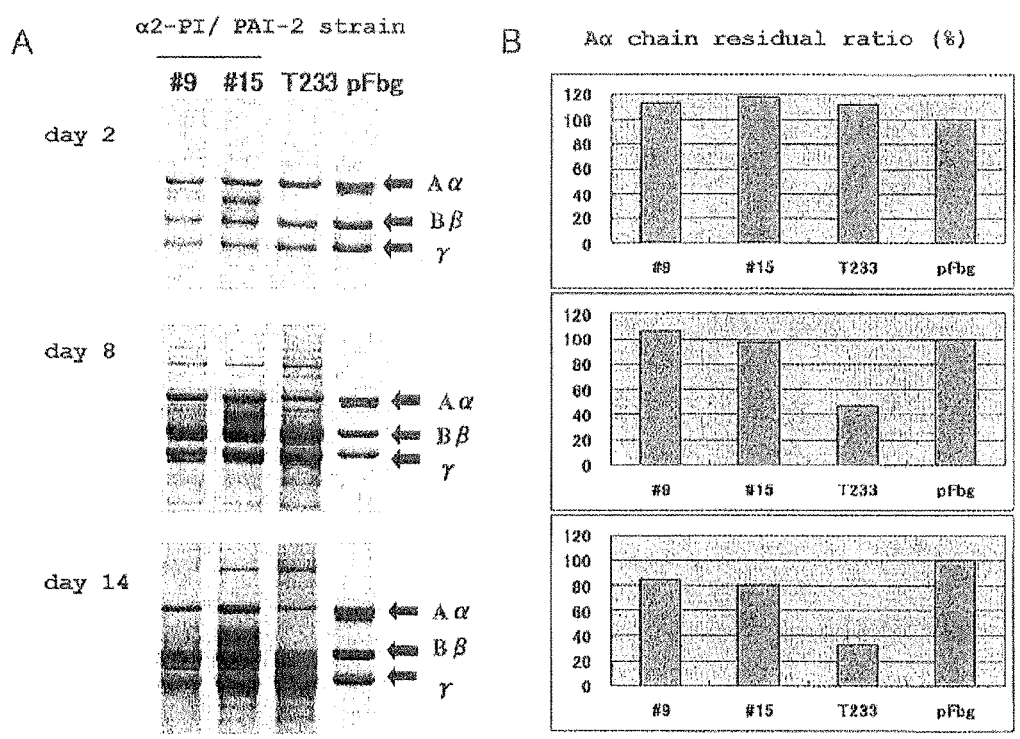
FIG. 9 shows suppression of degradation of fibrinogen in coexpressing cell strains α2PI/PAI-2/T233 #9 and #15. Fibrinogen expressing cell strain T233, and coexpressing cell strains α2PI/PAI-2/T233 #9 and #15 were cultured for 2 days, 8 days and 14 days, the culture supernatants were subjected to SDS-PAGE under reducing conditions, and gel after electrophoresis was stained with Instant Blue staining solution (manufactured by Funakoshi Co., Ltd., ISB1L) for 15 min.

1. Suppression of Degradation of Fibrinogen Aα Chain in Coexpressing Cell Strain Established Using α2PI/PAI-2/pcDNA3.3-Modified Fibrinogen expressing cell strain T233, and coexpressing cell strains α2PI/PAI-2/T233 #9 and #15 were each suspended in Fed-Batch medium (Table 3) at a high cell density of 1×10⁶ cells/mL, 5 mL thereof was seeded in a 125 mL flask and cultured by shaking the flask for 2 weeks (37° C., 5% CO₂, 120-140 rpm). The culture supernatants (10 μL) on day 2, day 8 and day 14 were subjected to SDS-PAGE under reducing conditions, and the gel after electrophoresis was stained with Instant Blue staining solution (manufactured by Funakoshi Co., Ltd., ISB1L) for 15 min. In fibrinogen in the culture supernatant of the fibrinogen expressing cell strain T233, the ratio of Aα chain (67 kDa) decreased along with an increasing number of culture day as compared to fibrinogen Bβ chain (56 kDa) and γ chain (48 kDa), and it was clarified that the degradation of fibrinogen Aα chain proceeds as the culture period becomes longer (FIG. 9A). On the other hand, fibrinogen γ chain was scarcely degraded irrespective of the high/low number of culture period, and therefore, the stained gel was scanned by a densitometer (manufactured by Bio-Rad, Calibrated Densitometer GS-800), and variation of Aα chain relative to γ chain was shown in numerical values. To be specific, using the attached software "Quantity One", the band volume (band concentration×area) of Aα chain, Bβ chain and γ chain was each measured, and the ratio of Aα chain was calculated by dividing the band volume of Aα chain by the band volume of γ chain (molecular weight: Aα chain 67 kD, γ chain 48 kD). The ratio of Aα chain to γ chain in the plasma-derived fibrinogen (pFbg: manufactured by CALBIOCHEM, 341576) simultaneously electrophoresed as a control in each gel was used as an index of degradation. The relative value of the ratio of Aα chain to γ chain in each culture sample when the ratio of Aα chain to γ chain of pFbg is 100% is shown as the Aα chain residual ratio (FIG. 9B).

As a result, on day 2 of culture, the Aα chain residual ratio of fibrinogen expressing cell strain T233, and coexpressing cell strains α2PI/PAI-2/T233 #9 and #15 was equal to the Aα chain residual ratio of the control pFbg, and degradation of fibrinogen Aα chain was not observed in any cell strain. However, on day 8 of culture, the Aα chain residual ratio of the fibrinogen expressing cell strain T233 decreased to not more than half (47%) of the Aα chain residual ratio of the control pFbg, and remarkable degradation of fibrinogen Aα chain was found. The Aα chain residual ratio of the coexpressing cell strains α2PI/PAI-2/T233 #9 and #15 maintained at least the same level (97-106%) as the Aα chain residual ratio of the control pFbg, similar to that on day 2 of culture, and degradation of fibrinogen Aα chain was hardly found. On day 14 of culture, the Aα chain residual ratio of the fibrinogen expressing cell strain T233 decreased to about ⅓ (33%) of the Aα chain residual ratio of the control pFbg, and degradation of fibrinogen Aα chain progressed further than on day 8 of culture. The Aα chain residual ratio of the coexpressing cell strains α2PI/PAI-2/T233 #9 and #15 slightly decreased (80-85%) as compared to day 8 of culture (97-106%) but still maintained the high Aα chain residual ratio. The Aα chain residual ratio was not less than about 2.5 times that (33%) of fibrinogen expressing cell strain T233 under the same conditions (FIG. 9B).

From the foregoing results, it was clarified that the residual ratio of Aα chain increases by not less than about 2.5-fold, even in the later stage of culture when cell density is high and degradation of fibrinogen generally proceeds markedly, since degradation of fibrinogen Aα chain in the culture is strongly suppressed as compared to the expression of fibrinogen alone, by coexpression of fibrinogen and α2PI and/or PAI-2.

2. Suppression of Degradation of Fibrinogen Aα Chain in Coexpressing Cell Strain Established Using α2PI/PAI-2/m-pEE Whether degradation of fibrinogen can be suppressed under high culture conditions of high cell density in a coexpressing cell strain established using expression vector α2PI/PAI-2/m-pEE different from α2PI/PAI-2/pcDNA3.3-modified was examined.

Figure 10:
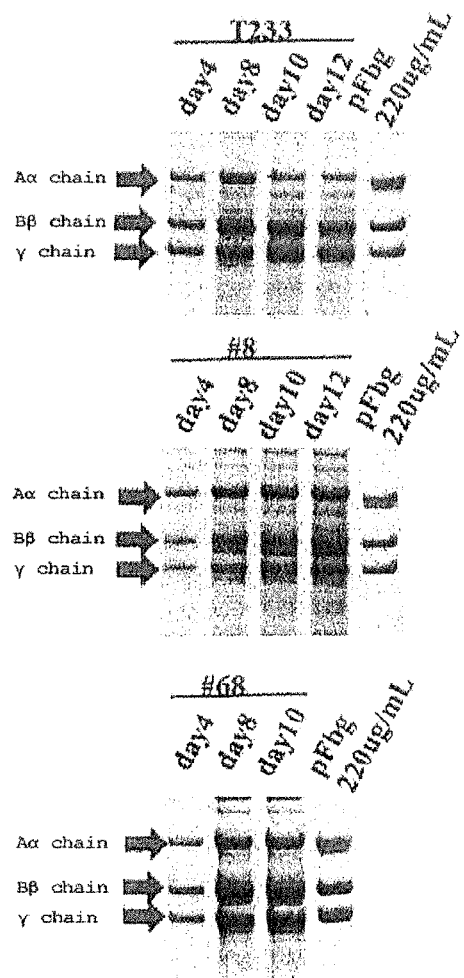
FIG. 10 shows suppression of degradation of fibrinogen in coexpressing cell strains α2PI/PAI-2/T233 #8 and #68. Fibrinogen expressing cell strain T233 and coexpressing cell strains α2PI/PAI-2/T233 #8 and #68 were each suspended in Fed-Batch medium at $1 \times 10^6$ cells/mL, 20 mL was seeded in a 125 mL flask, and flask culture with shaking was performed for 12 days (37° C., 5% $CO_2$, 120-140 rpm). The culture supernatants on day 4, day 8, day 10 and day 12 were analyzed. The culture supernatant (5 µL) was subjected to SDS-PAGE under reducing conditions, and gel after electrophoresis was stained with Instant Blue staining solution (manufactured by Funakoshi Co., Ltd., ISBIL) for 15 min.
Figure 10:
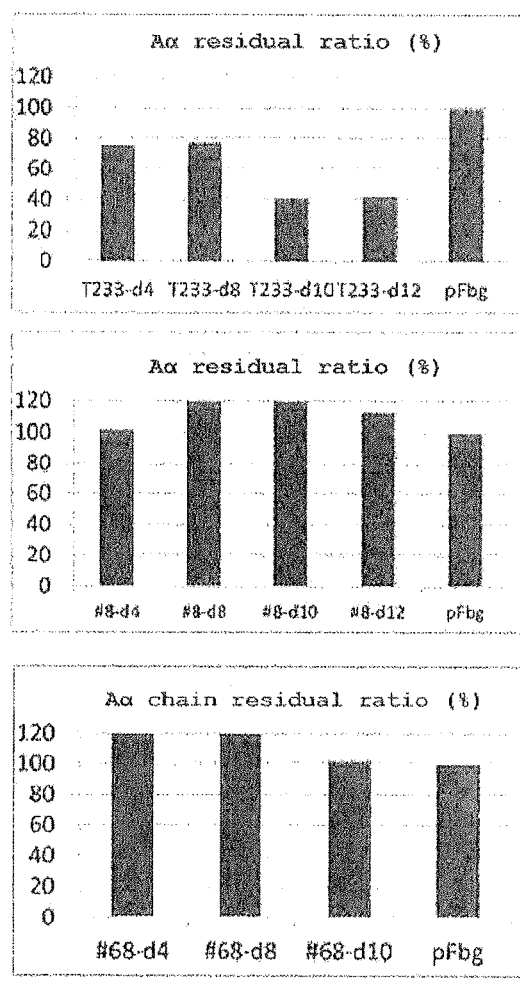

Similar to the method described in the above-mentioned Example 6, 1., fibrinogen expressing cell strain T233, and coexpressing cell strains α2PI/PAI-2/T233 #8 and #68 were each suspended in Fed-Batch medium (Table 3) at a high cell density of $1 \times 10^6$ cells/mL, 20 mL thereof was seeded in a 125 mL flask and cultured by shaking the flask for 12 days (37° C., 5% $CO_2$, 120-140 rpm). The culture supernatants (5 μL) on day 4, day 8, day 10 and day 12 were subjected to SDS-PAGE under reducing conditions, and the gel after electrophoresis was stained with Instant Blue staining solution (manufactured by Funakoshi Co., Ltd., ISB1L) for 15 min. As a result, similar to the results of the above-mentioned 1., in fibrinogen in the culture supernatant of the fibrinogen expressing cell strains T233, the ratio of Aα chain (67 kDa) decreased along with an increasing number of culture day as compared to fibrinogen Bβ chain (56 kDa) and γ chain (48 kDa), and it was clarified that the degradation of fibrinogen Aα chain proceeds as the culture period becomes longer (FIG. 10A). On the other hand, fibrinogen γ chain was scarcely degraded irrespective of the high/low number of culture period, and therefore, the stained gel was scanned by a densitometer (manufactured by Bio-Rad, Calibrated Densitometer GS-800), and variation of Aα chain relative to γ chain was shown in numerical values. To be specific, using the attached software "Quantity One", the band volume (band concentration×area) of Aα chain, Bβ chain and γ chain was each measured, and the ratio of Aα chain was calculated by dividing the band volume of Aα chain by the band volume of γ chain. The ratio of Aα chain to γ chain in the plasma-derived fibrinogen (pFbg: manufactured by CALBIOCHEM, 341576) simultaneously electrophoresed as a control in each gel was used as an index of degradation. The relative value of the ratio of Aα chain to γ chain in each culture sample when the ratio of Aα chain to γ chain of pFbg is 100% is shown as the Aα chain residual ratio (FIG. 10B).

As a result, on day 4 and day 8 of culture, the Aα chain residual ratio of fibrinogen expressing cell strain T233, and coexpressing cell strains α2PI/PAI-2/T233 #8 and #68 was not less than about 80%, and degradation of fibrinogen Aα chain was hardly observed in any cell strain. However, on day 10 of culture, the Aα chain residual ratio of the fibrinogen expressing cell strain T233 decreased to not more than half (40%) of the Aα chain residual ratio of the control pFbg, and remarkable degradation of fibrinogen Aα chain was found. The Aα chain residual ratio of the coexpressing cell strains α2PI/PAI-2/T233 #8 and #68 maintained at least the same level (100% or more) as the Aα chain residual ratio of the control pFbg, and degradation of fibrinogen Aα chain was hardly found. The Aα chain residual ratio was not less than about 2.5 times that of fibrinogen expressing cell strain T233 under the same conditions (FIG. 10B).

The suppressive effect on degradation of fibrinogen in the coexpressing cell strain established using the above α2PI/PAI-2/m-pEE matched with the effect in the coexpressing cell strain established using α2PI/PAI-2/pcDNA3.3-modified.

When fibrinogen was coexpressed with α2PI and PAI-2, mRNA expression levels of α2PI and PAI-2 varied due to the difference in α2PI and PAI-2 transgene vectors, or difference in the obtained cell strains (Example 5). Nevertheless, the fibrinogen residual ratio of Aα chain in the coexpressing cell strain was similarly high (about 2.5 fold) as compared to the Aα chain residual ratio of fibrinogen expressing cell strain T233 under the same conditions, irrespective of the vector used and in any cell strain, under the same conditions.

These results show that the suppressive effect on degradation of fibrinogen Aα chain in coexpressing cell strain is not significantly influenced by the high or low level of mRNA expression of α2PI and PAI-2, or difference in the expression vectors and cell strains.

Example 7: Suppression of Plasmin-Like Protease Activity in the Culture Supernatant Fibrinogen expressing cell strain T233, and coexpressing cell strains α2PI/PAI-2/T233 #9 and #15 were cultured under the same conditions as in Example 6, and the plasmin-like activity in the culture supernatant was measured on day 14 of culture by using a Test Team (registered trade mark) PLG 2 kit (manufactured by SEKISUI MEDICAL CO., LTD., 439-9091). To be specific, culture supernatant (50 μL) and chromogenic synthetic substrate S-2251 for plasmin (highly specific to plasmin-like active substance) (50 μL) were mixed and the mixture was stood at 37° C. for 24 hr. A reaction quenching liquid (1 mL) was added, and the absorbance was measured by a spectrophotometer at wavelength 405 nm. The absorbance of coexpressing cell strains α2PI/PAI-2/T233 #9 and #15 when the absorbance of fibrinogen expressing cell strain T233 is 1 is shown as relative value (FIG. 11).

As a result, the relative absorbance of coexpressing cell strains α2PI/PAI-2/T233 #9 and #15 to the absorbance of fibrinogen expressing cell strain T233 is 0.5 and 0.2, respectively, and it was clarified that the plasmin-like protease activity in the culture supernatant was suppressed to at least half.

Figure 11:
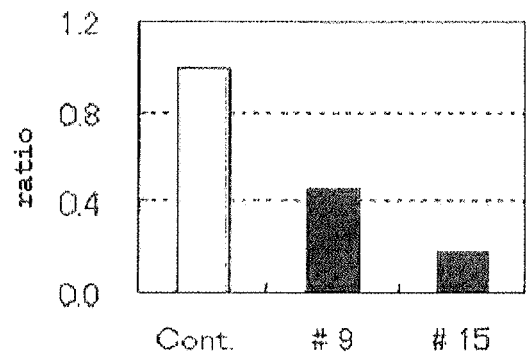
FIG. 11 shows a plasmin-like protease activity in the culture supernatant after culture of fibrinogen expressing cell strain T233, and coexpressing cell strains α2PI/PAI-2/T233 #9 and #15 for 14 days. The absorbance of coexpressing cell strains α2PI/PAI-2/T233 #9 and #15 is shown as a relative value when the absorbance of Fibrinogen expressing cell strain T233 is 1.

In the coexpressing cell strains α2PI/PAI-2/T233 #9 and #15, degradation of fibrinogen Aα chain was strongly suppressed even in the later stage of culture when cell density is high and degradation of fibrinogen generally proceeds markedly (FIG. 9), and the plasmin-like activity was also suppressed (FIG. 11). Therefore, the possibility was suggested that the degradation of fibrinogen Aα chain was suppressed since the production and activity of plasmin present in the culture supernatant was inhibited by the coexpressed α2PI and PAI-2.

Example 8: Production of Fibrinogen in Coexpressing Cell Strains α2PI/PAI-2/T233 #9 and #15)

As mentioned above, degradation of fibrinogen generally progresses markedly in the later stage of culture when the cell density is high, and scarcely progress in the initial stages when the cell density is low. Therefore, fibrinogen expressing cell strain T233, and coexpressing cell strains α2PI/PAI-2/T233 #9 and #15 were cultured under culture conditions with low cell density at which degradation of fibrinogen does not occur easily, and whether coexpression of fibrinogen and α2PI and PAI-2 influences the fibrinogen producibility independent of the suppressive effect on degradation of fibrinogen was examined.

Fibrinogen expressing cell strain T233, and coexpressing cell strains α2PI/PAI-2/T233 #9 and #15 were suspended in Batch medium (Table 3) at a low cell density of $1.2 \times 10^5$ cells/mL, 30 mL thereof was seeded in a 125 mL flask, and cultured by shaking the flask for 10 days (37° C., 5% $CO_2$, 120-140 rpm). The culture supernatant was sampled by 0.4 mL per day, and Fed-Batch medium 5% (v/v) was added on day 4 of culture. Then, the amount of fibrinogen in the culture supernatant was measured as follows by the ELISA method.

Anti-human fibrinogen•rabbit polyclonal antibody (manufactured by DAKO, A0080) (6 mg/ml) was diluted 1,200-fold with Coating Solution (manufactured by KPL, 50-84-01), added to a 96 well plate (manufactured by Coster, 3590) by 100 μL per well and stood at 4° C. overnight. Then, BSA Diluent/Blocking Solution (manufactured by KPL, 50-61-01) was added by 300 μL per well, and the mixture was stood at room temperature for 1 hr. A dilution series of plasma-derived fibrinogen (pFbg: manufactured by CALBIOCHEM, 341576) was produced and used as the standard (440 ng/mL, 220 ng/mL, 110 ng/mL, 55 ng/mL, 27.5 ng/mL, 13.75 ng/mL, 6.88 ng/mL, 3.44 ng/mL, 0 ng/mL). A standard and measurement sample was added by 100 μL per well, and the mixture was stood at room temperature for 1 hr. Then, the plate was washed with Washing Solution (300 μL/well, 5 times, using plate washer), secondary antibody solution diluted 10,000-fold with BSA Diluent/Blocking Solution was added by 100 μL per well, and the mixture was stood at room temperature for 1 hr. After washing with Washing Solution (0.05% Tween80, 0.9% NaCl), Detection Solution (manufactured by KPL, 50-62-00) was added by 100 μL per well, and the mixture was stood at room temperature for 10 min. Peroxidase Stop Solution (manufactured by KPL, 50-85-01) was added by 100 μL per well, and the reaction was discontinued. The absorbance was measured at wavelength 405 nm.

Figure 12:
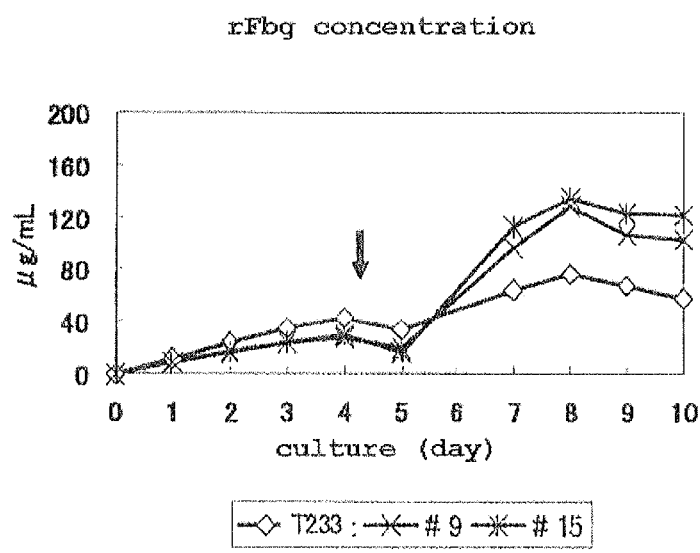
FIG. 12 shows time course changes of the production amount of fibrinogen when fibrinogen expressing cell strain T233, and coexpressing cell strains α2PI/PAI-2/T233 #9 and #15 were cultured under suppressing conditions for degradation of fibrinogen for 0-10 days.

As a result, the amount of fibrinogen in the culture supernatant showed a similar tendency up to day 5 of culture in all of fibrinogen expressing cell strain T233, and coexpressing cell strains α2PI/PAI-2/T233 #9 and #15, and the fibrinogen amount on day 4 of culture was about 40 μg/mL (FIG. 12). However, on day 8 of culture, the fibrinogen amount in fibrinogen expressing cell strain T233 was about 80 μg/mL, whereas the fibrinogen amount in coexpressing cell strains α2PI/PAI-2/T233 #9 and #15 reached about 150 μg/mL, thus showing about 2-fold fibrinogen amount as compared to fibrinogen expressing cell strain T233. Since degradation of fibrinogen scarcely progresses under the low cell density culture conditions in this Example, it was clarified from the results that coexpression of fibrinogen and α2PI and/or PAI-2 drastically increases (about 2-fold) the production amount of fibrinogen independently of the suppressive effect on degradation of fibrinogen.

Example 9: Production of Fibrinogen in Coexpressing Cell Strains α2PI/PAI-2/T233 #8 and #68)

As for coexpressing cell strains α2PI/PAI-2/T233 #8 and #68 established using a vector different from coexpressing cell strains α2PI/PAI-2/T233 #9 and #15, fibrinogen expressing cell strain T233, and coexpressing cell strains α2PI/PAI-2/T233 #8 and #68 were cultured under culture conditions with low cell density at which degradation of fibrinogen does not occur easily, and whether coexpression of fibrinogen and α2PI and PAI-2 influences the fibrinogen producibility independent of the suppressive effect on degradation of fibrinogen was examined.

Fibrinogen expressing cell strain T233, and coexpressing cell strains α2PI/PAI-2/T233 #8 and #68 were suspended in Batch medium (Table 3) at a low cell density of $2 \times 10^5$ cells/mL, 20 mL thereof was seeded in a 125 mL flask, and cultured by shaking the flask for 8 days (37° C., 5% $CO_2$, 120-140 rpm). The culture supernatant was sampled by 0.4 mL per day, and an equal amount of Fed-Batch medium was added.

Figure 13:
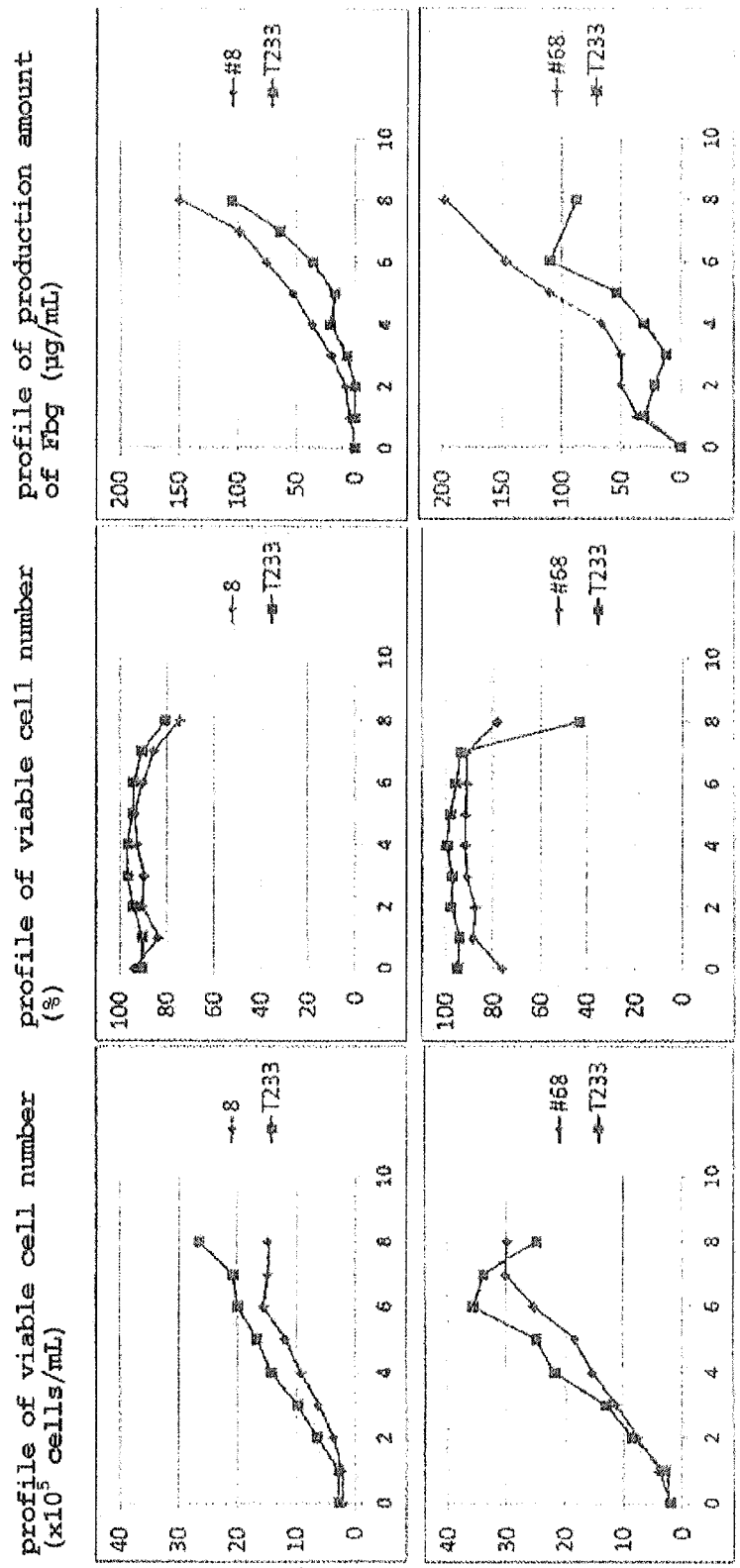
FIG. 13 shows time course changes of the viable cell number, cell survival rate and production amount of fibrinogen when fibrinogen expressing cell strain T233, and coexpressing cell strains α2PI/PAI-2/T233 #8 and #68 were cultured under suppressing conditions for degradation of fibrinogen for 0-10 days.

Fibrinogen expressing cell strain T233, and coexpressing cell strains α2PI/PAI-2/T233 #8 and #68 did not show a large difference in the profile of the viable cell number and survival rate (FIG. 13).

Then, by a method similar to that in Example 8, the fibrinogen amount in the culture supernatant was measured by the ELISA method. As a result, the fibrinogen amount in the culture supernatant of coexpressing cell strains α2PI/PAI-2/T233 #8 and #68 was different from the profile of the viable cell number, and high fibrinogen amount profile was observed from day 3 of culture, as compared to fibrinogen expressing cell strain T233. On day 8 of culture, the fibrinogen amount of fibrinogen expressing cell strain T233 was about 100 μg/mL, whereas it was about 150 μg/mL in coexpressing cell strain α2PI/PAI-2/T233 #8, and about 200 μg/mL in #68, thus showing an about 1.5- to 2-fold fibrinogen amount as compared to fibrinogen expressing cell strain T233.

These results show that coexpression of fibrinogen with α2PI and PAI-2 can enhance fibrinogen producibility independently of the suppressive effect on degradation of fibrinogen. Furthermore, it was clarified that the effect is free from an influence of a difference in vectors and cell strains.

From the foregoing, it was shown that a recombinant strain highly producing fibrinogen produced by the method of the present invention strongly suppresses degradation of fibrinogen even in the later stage of culture when degradation of fibrinogen generally progresses, as a result of which increases the residual ratio of fibrinogen Aα chain to about 2.5-fold or more as compared to, for example, a cell strain expressing fibrinogen alone, as well as increases (about 1.5- to 2-fold) the production amount of fibrinogen independent of the suppressive effect on degradation of fibrinogen. Due to a synergistic effect of these, at least not less than about 4-fold production amount of fibrinogen can be achieved as compared to a cell strain expressing fibrinogen alone.

Example 10: Suppressive Effect on Degradation of Fibrinogen by Addition of α2PI, PAI-1 and PAI-2)

The results of Example 6 have clarified that coexpression of fibrinogen with α2PI and PAI-2 can strongly suppress degradation of fibrinogen in the later stage of culture. To confirm whether the coexpressed two kinds of proteins both afford a suppressive effect on degradation, and whether use of PAI-1 having similar action mechanism as PAI-2 affords a suppressive effect on degradation of fibrinogen, α2PI, PAI-1 and PAI-2 were each added to the culture supernatant of fibrinogen expressing cell strain T233 in the later stage of culture, and variation in the ratio of Aα chain to fibrinogen γ chain was examined.

Figure 14:
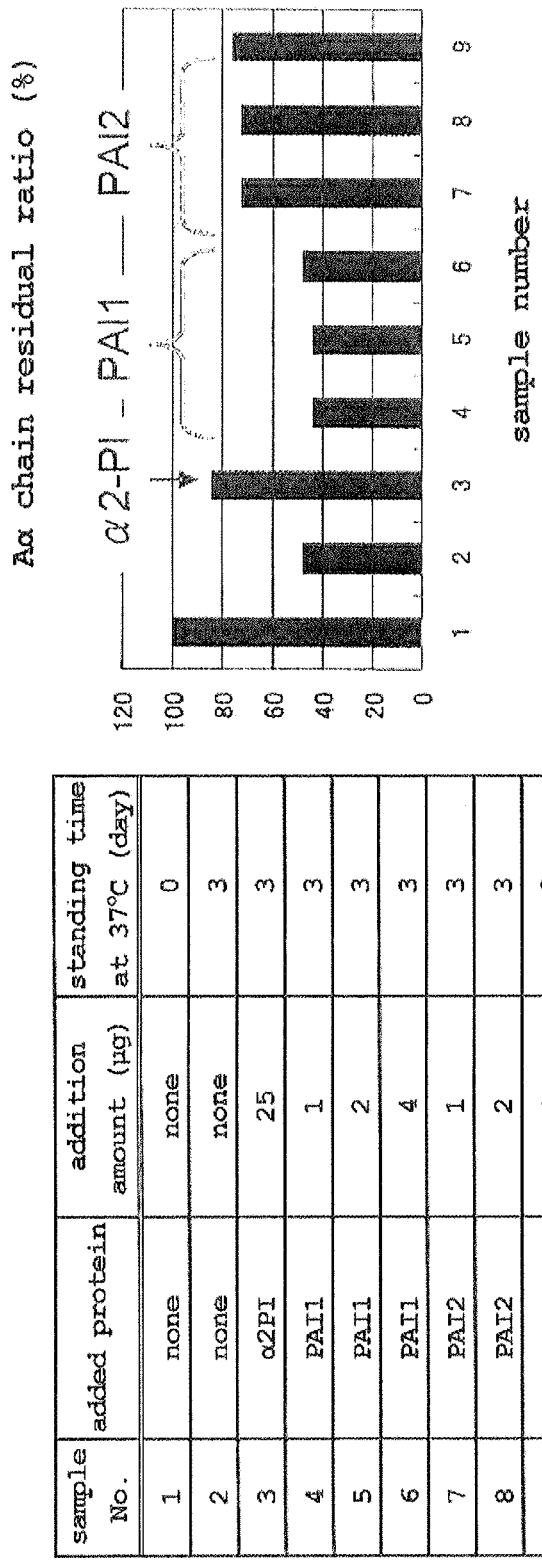
FIG. 14 shows variation in the fibrinogen Aα chain in numerical values when fibrinogen expressing cell strain T233 was cultured for 10 days, α2PI, PAI-1 and PAI-2 were each added to the culture supernatant and stood at 37° C. for 3 days, and shows a suppressive effect on degradation of fibrinogen by the addition of α2PI and PAI-2. The relative value of the ratio of Aα chain to γ chain in each culture sample when the ratio of Aα chain to γ chain in fibrinogen expressing cell strain T233 on day 10 of culture is 100% is shown as the Aα chain residual ratio.

Fibrinogen expressing cell strain T233 was suspended in Fed-Batch medium (Table 3) at a high cell density of $1\times10^6$ cells/mL, 5 mL thereof was seeded in a 125 mL flask and cultured by shaking the flask for 10 days (37° C., 5% $CO_2$, 120-140 rpm). α2PI (manufactured by Abcam, ab90921), PAI-1 (manufactured by Pepro tech, 140-04) or PAI-2 (manufactured by Pepro tech, 140-06) was added to the culture supernatant (100 μL) on day 10 of culture, or without addition thereof, and the cells were further stood at 37° C. for 3 days. The amount of α2PI and PAI-2 added was equal to the amount expressed in the culture supernatants of coexpressing cell strains α2PI/PAI-2/T233 #9 and #15 on day 10 of culture. The amount of PAI-1 added followed the amount of PAI-2. The relative value of the ratio of Aα chain to γ chain in each culture sample when the ratio of Aα chain to γ chain in fibrinogen expressing cell strain T233 on day 10 of culture is 100% is shown as the Aα chain residual ratio (FIG. 14).

As a result, degradation progressed when fibrinogen expressing cell strain T233 on day 10 of culture was stood under non-addition conditions at 37° C. for 3 days, and the Aα chain residual ratio reached 48%. When α2PI or PAI-2 was added to fibrinogen expressing cell strain T233 on day 10 of culture and stood at 37° C. for 3 days, the Aα chain residual ratio reached 72-84%, and degradation of fibrinogen was suppressed as compared to non-addition (48%). Since both α2PI and PAI-2 suppressed degradation of fibrinogen, it was clarified that each has a suppressive effect on the degradation of fibrinogen Aα chain. On the other hand, the Aα chain residual ratio when PAI-1, which is a protein similar to PAI-2, was added and the mixture was stood at 37° C. for 3 days was of the same level (44-48%) as non-addition (48%), and a suppressive effect on degradation of fibrinogen was not found in PAI-1 (FIG. 14).

Both PAI-1 and PAI-2 are inhibitors belonging to SERPIN and present in vivo, which suppress plasmin production from plasminogen by inhibiting a plasminogen activator. The large difference in the effects by the addition of protease inhibitory proteins, PAI-1 and PAI-2, having similar action mechanism indicates that the mechanism involved in the degradation of fibrinogen Aα chain has exact specificity.

INDUSTRIAL APPLICABILITY

The recombinant strain highly producing fibrinogen of the present invention that strongly suppresses degradation of fibrinogen even in the later stage of culture when degradation of fibrinogen generally proceeds can not only increase the residual ratio of fibrinogen Aα chain by not less than about 2.5-fold compared to, for example, a cell strain expressing fibrinogen alone, but also can increase (about 1.5- to 2-fold) the production amount of fibrinogen, independent of the suppressive effect on degradation of fibrinogen. As a result of the synergistic effect thereof, the production amount of fibrinogen is not less than about 4-fold that of a cell strain expressing fibrinogen alone. Therefore, using the recombinant strain highly producing fibrinogen of the present invention, a recombinant fibrinogen can be produced in a large amount, a recombinant fibrinogen can be formulated at a practical level, and stable supply of fibrinogen to the market can be secured.

Furthermore, since fibrinogen obtained by the recombinant strain highly producing fibrinogen of the present invention is produced by a gene recombination technique, the risk of contamination with infectious agents, which is a problem specific to a preparation derived from blood, can be eliminated completely, and sufficient safety can be secured. Consequently, fibrinogen in an amount sufficient for the treatment can be used safely, and securely for a long term.

This application is based on patent application No. 2013-273145 filed in Japan (filing date: Dec. 27, 2013), the contents of which are incorporated in full herein.

The invention claimed is:

1. A recombinant animal cell comprising genes encoding the Aα chain, Bβ chain, and γ chain of fibrinogen and gene(s) encoding α2 plasmin inhibitor (α2PI) and/or plasminogen activator inhibitor-2 (PAI-2), wherein functional fibrinogen is produced by coexpressing said fibrinogen genes with α2PI and/or PAI-2 in said animal cell, and wherein said cell suppresses degradation of fibrinogen during cell culture and/or increases the production amount of fibrinogen independent of the suppressive effect, compared to the same animal cell expressing fibrinogen but which does not coexpress α2PI and/or PAI-2.

2. The recombinant cell according to claim 1, wherein the fibrinogen and α2PI and/or PAI-2 are human fibrinogen and human α2PI and/or PAI-2.

3. The recombinant cell according to claim 1, wherein the animal cell is a Chinese hamster ovary (CHO) cell strain.

4. A method of making a recombinant animal cell that produces fibrinogen, comprising introducing genes encoding Aα chain, Bβ chain and γ chain of fibrinogen, and gene(s) encoding a2 plasmin inhibitor (a2PI) and/or plasminogen activator inhibitor-2 (PAI-2) into an animal cell, and coexpressing the fibrinogen and a2PI and/or PAI-2 in the animal cell, wherein said cell suppresses degradation of fibrinogen during cell culture and/or increases the production amount of fibrinogen independent of the suppressive effect, compared to an animal cell expressing fibrinogen but which does not coexpress α2PI and/or PAI-2.

5. The method according to claim 4, comprising expressing fibrinogen in the animal cell by using a single expression vector comprising all of genes encoding Aα chain, Bβ chain and γ chain of fibrinogen.

6. The method according to claim 4, comprising expressing α2PI and PAI-2 in the animal cell by using a single expression vector comprising a gene encoding α2PI and a gene encoding PAI-2.

7. The method according to claim 4, wherein the genes encoding Aα chain, Bβ chain and γ chain of fibrinogen and the gene(s) encoding α2PI and/or PAI-2 are each a human gene.

8. The method according to claim 4, wherein the animal cell is a CHO cell.

9. A production method of a recombinant fibrinogen, comprising culturing the recombinant animal cell according to claim 1 in a medium, and recovering fibrinogen from the obtained culture.

10. A production method of a recombinant fibrinogen, comprising culturing the fibrinogen producing recombinant animal cell, obtained by the method according to claim 4, in a medium, and recovering fibrinogen from the obtained culture.

* * * * *

SEQUENCE LISTING

```
<160> NUMBER OF SEQ ID NOS: 20

<210> SEQ ID NO 1
<211> LENGTH: 30
<212> TYPE: DNA
<213> ORGANISM: Artificial Sequence
<220> FEATURE:
<223> OTHER INFORMATION: primer

<400> SEQUENCE: 1
ggaagcttgc caccatgttt tccatgagga                                    30

<210> SEQ ID NO 2
<211> LENGTH: 30
<212> TYPE: DNA
<213> ORGANISM: Artificial Sequence
<220> FEATURE:
<223> OTHER INFORMATION: primer

<400> SEQUENCE: 2
ggcccgggct agacagggcg agatttagca                                    30
```

```
<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
ggaagcttgc caccatgaaa catctattat                                30

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
gggaattcct attgctgtgg gaagaagggc                                30

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
ggaagcttgc caccatgagt tggtccttgc                                30

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
gggaattctt aaacgtctcc agcctgtttg                                30

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
ccctatggtc gactctcagt acaatctg                                  28

<210> SEQ ID NO 8
<211> LENGTH: 28
<212> TYPE: DNA
<213> ORGANISM: Artificial Sequence
<220> FEATURE:
<223> OTHER INFORMATION: primer

<400> SEQUENCE: 8
gatccgtcga cgtcaggtgg cactttc                                   28

<210> SEQ ID NO 9
<211> LENGTH: 33
<212> TYPE: DNA
<213> ORGANISM: Artificial Sequence
<220> FEATURE:
<223> OTHER INFORMATION: primer
```

<400> SEQUENCE: 9
gctggtaccc gatcctctag agtccggagg ctg            33

<210> SEQ ID NO 10
<211> LENGTH: 34
<212> TYPE: DNA
<213> ORGANISM: Artificial Sequence
<220> FEATURE:
<223> OTHER INFORMATION: primer

<400> SEQUENCE: 10
aatttcgaat accggttagt aatgagttta aacg           34

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
cttctcgagc gatcctctag agtccggagg ctg            33

<210> SEQ ID NO 12
<211> LENGTH: 34
<212> TYPE: DNA
<213> ORGANISM: Artificial Sequence
<220> FEATURE:
<223> OTHER INFORMATION: primer

<400> SEQUENCE: 12
gctaagcttt accggttagt aatgagttta aacg           34

<210> SEQ ID NO 13
<211> LENGTH: 42
<212> TYPE: DNA
<213> ORGANISM: Artificial Sequence
<220> FEATURE:
<223> OTHER INFORMATION: primer

<400> SEQUENCE: 13
aacctcgagg ccgccaccat ggaggatctt tgtgtggcaa ac  42

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14
gggaagctta gggtgaggaa aatctgccg                 29

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
aaaggtaccg ccgccaccat ggcgctgctc tggggctcc     40

<210> SEQ ID NO 16
<211> LENGTH: 34

```
<212> TYPE: DNA
<213> ORGANISM: Artificial Sequence
<220> FEATURE:
<223> OTHER INFORMATION: primer

<400> SEQUENCE: 16
cccttcgaat cacttggggc tgccaaactg gggg                                34

<210> SEQ ID NO 17
<211> LENGTH: 40
<212> TYPE: DNA
<213> ORGANISM: Artificial Sequence
<220> FEATURE:
<223> OTHER INFORMATION: primer

<400> SEQUENCE: 17
aacctcgagg ccgccaccat ggtgctgctc tgggggctcc                          40

<210> SEQ ID NO 18
<211> LENGTH: 34
<212> TYPE: DNA
<213> ORGANISM: Artificial Sequence
<220> FEATURE:
<223> OTHER INFORMATION: primer

<400> SEQUENCE: 18
cccggtacct cacttggggc tgccaaactg gggg                                34

<210> SEQ ID NO 19
<211> LENGTH: 42
<212> TYPE: DNA
<213> ORGANISM: Artificial Sequence
<220> FEATURE:
<223> OTHER INFORMATION: primer

<400> SEQUENCE: 19
aacaagcttg ccgccaccat ggaggatctt tgtgtggcaa ac                       42

<210> SEQ ID NO 20
<211> LENGTH: 31
<212> TYPE: DNA
<213> ORGANISM: Artificial Sequence
<220> FEATURE:
<223> OTHER INFORMATION: primer

<400> SEQUENCE: 20
gggttcgaat tagggtgagg aaaatctgcc g                                   31
```